(12) United States Patent
Sakamoto et al.

(10) Patent No.: US 11,185,638 B2
(45) Date of Patent: Nov. 30, 2021

(54) NEEDLE ASSEMBLY AND NEEDLE DEVICE HAVING SAME

(71) Applicant: NIPRO CORPORATION, Osaka (JP)

(72) Inventors: Shingo Sakamoto, Osaka (JP); Asumi Mino, Osaka (JP)

(73) Assignee: NIPRO CORPORATION, Osaka (JP)

( * ) Notice: Subject to any disclaimer, the term of this patent is extended or adjusted under 35 U.S.C. 154(b) by 279 days.

(21) Appl. No.: 16/465,857

(22) PCT Filed: Dec. 4, 2017

(86) PCT No.: PCT/JP2017/043467
§ 371 (c)(1),
(2) Date: May 31, 2019

(87) PCT Pub. No.: WO2018/101482
PCT Pub. Date: Jun. 7, 2018

(65) Prior Publication Data
US 2019/0298933 A1    Oct. 3, 2019

(30) Foreign Application Priority Data

Dec. 2, 2016  (JP) .............................. JP2016-234785
Jul. 14, 2017  (JP) .............................. JP2017-138291

(51) Int. Cl.
*A61M 5/32*    (2006.01)

(52) U.S. Cl.
CPC ............ *A61M 5/3202* (2013.01); *A61M 5/32* (2013.01); *A61M 5/3216* (2013.01); *A61M 5/3293* (2013.01); *A61M 2005/3217* (2013.01)

(58) Field of Classification Search
CPC ................ A61M 5/321; A61M 5/3216; A61M 2005/3217
See application file for complete search history.

(56) References Cited

U.S. PATENT DOCUMENTS 5,665,075 A    9/1997  Gyure et al.
8,057,431 B2 *  11/2011  Woehr ................ A61M 5/3216
                                                     604/110

(Continued)

FOREIGN PATENT DOCUMENTS

| JP | H10-57489 A | 3/1998 |
| JP | 5896927 B2 | 3/2016 |
| WO | 2016002389 A1 | 1/2016 |

*Primary Examiner* — Laura A Bouchelle
(74) *Attorney, Agent, or Firm* — Alleman Hall Creasman & Tuttle LLP

(57) ABSTRACT

This needle assembly is provided with a needle having a needle tip, a needle hub, and a protector. The protector is displaceable between a non-protection position at which the needle is exposed and a protection position at which the needle tip is covered; has an opening formed elongated to match the needle, and includes a main body and a claw-like portion. The needle enters the main body from the opening to cover the needle tip when the protector is displaced to the protection position. The claw-like portion is bent by the needle when the protector is displaced to the protection position, allows the needle to advance into the main body, and is elastically restored to lock the needle when the needle enters the main body. The claw-like portion projects obliquely from the main body, extends across the opening in the width direction, and extends in the longitudinal direction.

12 Claims, 15 Drawing Sheets

(56) References Cited

U.S. PATENT DOCUMENTS

2013/0331793 A1 12/2013 Gonzales et al.
2015/0342639 A1 12/2015 Wang
2016/0220766 A1* 8/2016 Kawano .............. A61M 5/3213

* cited by examiner

NEEDLE ASSEMBLY AND NEEDLE DEVICE HAVING SAME

TECHNICAL FIELD

The present invention relates to a needle assembly configured to be capable of protecting a needle tip after use, and a needle device including the needle assembly.

BACKGROUND ART

A needle assembly is used at the time of infusion and blood collection, and safety needle assemblies such as Patent Literature 1 and Patent Literature 2 are known as an example of the needle assembly. In the safety needle assembly of Patent Literature 1, a collar is attached to a hub to which a cannula is fixed, and a sheath is pivotably attached to the collar. The sheath can be pivoted toward the cannula such that the cannula enters the groove in the sheath to protect the needle tip of the cannula. Further, the sheath is provided with a locking projection so as to close part of the groove, and the cannula is configured to bend the locking projection into the groove. The locking projection, on the other hand, locks the cannula as the cannula enters the groove, and stops the cannula from moving outward out of the groove.

Further, in the safety needle assembly of Patent Literature 2, a fixing tab corresponding to the locking projection of Patent Literature 1 is provided. The fixing tab is configured to bend, such that the cannula is locked to the fixing tab as the cannula passes over the bended fixing tab so that the cannula is locked. In addition, a hole is formed in the back wall of the sheath in order to form the fixing tab configured as described above.

CITATION LIST

Patent Literature

PTL 1: WO 2016/002389 A
PTL 2: 5896927 B1

SUMMARY OF INVENTION

Technical Problem

In the safety needle assembly of Patent Literature 1, as described above, when the cannula is put in the groove, it is necessary to bend the locking projection. The leverage principle is used in bending the locking projection. That is, the ease of bending is adjusted by regulating the distance from the fulcrum (base end of the locking projection) of the locking projection to the force point (the contact position of the locking projection and the cannula). Therefore, in order to facilitate the bending, a certain distance between the fulcrum and the force point is required. As a result, the locking projection becomes long, and the width of the groove is required to be wide. As a result, the outer dimension of the sheath is large. The increase in sheath outer dimension results in bulky disposal of the safety needle assembly. Therefore, in the needle assembly, it is required to reduce the outer dimension of the protector corresponding to the sheath.

Further, in the safety needle assembly of Patent Literature 2, since the cannula is locked so that the cannula does not come out of the sheath, the lock on the cannula can not basically be released. Therefore, with the cannula locked, if the sheath is pivoted away from the hub, for example by applying an unexpected load on the sheath, the cannula receives a load from the fixing tab such that the distal end is bent to the back wall. The cannula which receives such a load is different in length and needle diameter depending on the application, and a cannula which is shorter and thinner than the cannula described in Patent Literature 2 may be used, for example, when the amount of liquid injected and collected is small. When a cannula having such a shape is used, the load from the fixing tab causes the cannula to bend and be deformed such that the distal end of the cannula is directed toward the back wall of the sheath and approaches the hole. As long as the cannula is long as in the safety needle assembly of Patent Literature 2, there is no problem, but if the cannula is short enough that the distal end of the cannula, that is, the needle tip is located near the hole, the following event will occur. That is, as the cannula is bent and the distal end of the cannula approaches the hole, the distal end eventually falls into the hole. Also, as the distal end of the cannula is directed to the back wall, the distal end falls into the hole.

Also, if a short cannula is used, the following event may occur. That is, the cannula of metallic material may undergo plastic deformation when bent as described above, leaving the distal end facing the back wall. In this state, when a load is applied to the back wall of the sheath and the sheath pivots in the direction toward the hub, the distal end of the cannula may fall into a hole in the back wall or the like depending on the degree of plastic deformation of the cannula and the length of the cannula. In this way, in the safety needle assembly of Patent Literature 2, when a load is applied to the sheath (that is, the protector), the distal end (that is, the needle tip of the needle) of the cannula falls behind the hole (that is, the window).

Then, a first object of the present invention is to provide the needle assembly which can attain size reduction of a protector, and a needle device provided with the same.

A second object of the present invention is to provide a needle assembly capable of suppressing entry of a needle tip of a needle into the back of a window formed on the back face portion of a protector, and a needle device provided with the same.

Solution to Problem

In order to achieve the first object, a needle assembly of the present invention includes a needle formed elongated and having a sharp needle tip at a tip end, a needle hub provided at a base end of the needle, and a protector is provided on the needle hub so as to be displaceable between a non-protection position at which the needle is exposed and a protection position at which the needle tip is protected by covering the needle. The protector includes a protector main body having an opening formed elongated to match the needle, and allowing the needle to enter the protector main body from the opening to cover the needle tip when the protector is relatively displaced from the non-protection position to the protection position, and a claw-like portion provided on the protector main body such that the claw-like portion is bent by the needle when the protector is relatively displaced from the non-protection position to the protection position, allows the needle to advance into the protector main body, and is elastically restored to lock the needle when the needle enters the protector main body, and to stop the needle from escaping from an inside of the protector main body. The claw-like portion projects obliquely from the protector main body so as to extend across the opening in a width direction of the opening, and extend in a longitudinal direction of the opening.

According to the present invention, the portion where the needle contacts the claw-like portion can be shifted in one side or the other side in the longitudinal direction. By this, compared to the claw-like portion not extending in the longitudinal direction, it is possible to secure the distance from the starting point (for example, the base end of the claw-like portion) of the bending to the contact point between the claw-like portion and the needle without increasing the length in the width direction of the claw-like portion. Therefore, it is possible to narrow the width of the opening, and to miniaturize the protector main body.

In order to achieve the second object, a needle assembly includes: a needle having a sharp needle tip at a tip end; a needle hub provided at a base end of the needle; and a protector formed elongated to cover the needle, and provided on the needle hub so as to be displaceable between a non-protection position at which the needle is exposed and a protection position at which the needle tip is protected by covering the needle. The protector has an opening for the needle to enter the protector when relatively displaced from the non-protection position to the protection position in one of four directions orthogonal to a longitudinal direction and orthogonal to each other, and a pair of side face portions and a back face portion to cover the needle in the protection position in the remaining three directions. A window and at least one barrier are formed on the back face portion of the protector. The window is located near the needle tip of the needle when the protector is relatively displaced to the protection position. The at least one barrier is formed near the window, is located near the needle tip of the needle in the protection position, and projects from the back face portion so as to come into contact with the vicinity of the needle tip of the needle relatively displaced toward the window.

According to the present invention, by forming the barrier near the window, the needle can contact the barrier to stop the needle tip from reaching the window. This makes it possible to suppress entry of the needle tip into the back of the window.

Advantageous Effects of Invention

According to the present invention, the protector can be miniaturized.

Further, according to the present invention, it is possible to suppress the penetration of the needle tip of the needle into the back of the window formed in the back face portion of the protector.

DESCRIPTION OF EMBODIMENTS

Hereinafter, a needle assembly 1, 1A of the first and second embodiments according to the present invention and a needle device 2, 2A including the same will be described with reference to the drawings. In the following, the tip end of the needle assembly 1, 1A and the needle device 2, 2A is referred to as the distal end with respect to a user (i.e., the practitioner) who uses the needle device 2, 2A. The base end of the needle assembly 1, 1A and the needle device 2, 2A is referred to as the proximal end. The concept of the direction in the following description is used for convenience of the description, and the direction of the configuration of the invention is not limited to this direction. In addition, the needle assembly 1, 1A and the needle device 2, 2A described below are just one embodiment of the present invention. Accordingly, the present invention is not limited to the embodiments, and additions, deletions, and modifications are possible without departing from the spirit of the invention.

First Embodiment

[Needle Device]

Figure 1:
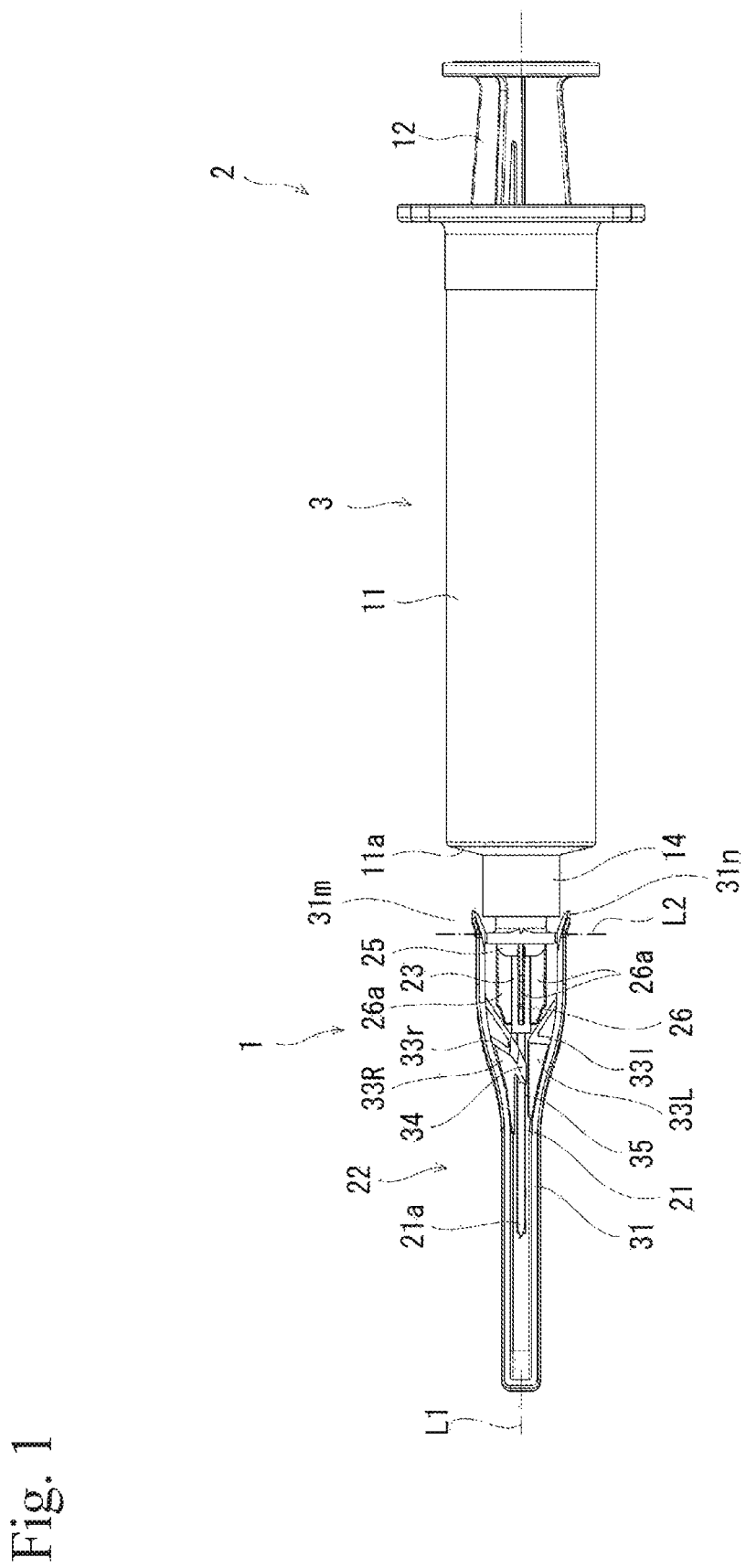
FIG. 1 is a front view of a needle device according to a first embodiment of the present invention as viewed from the side.
Figure 2:
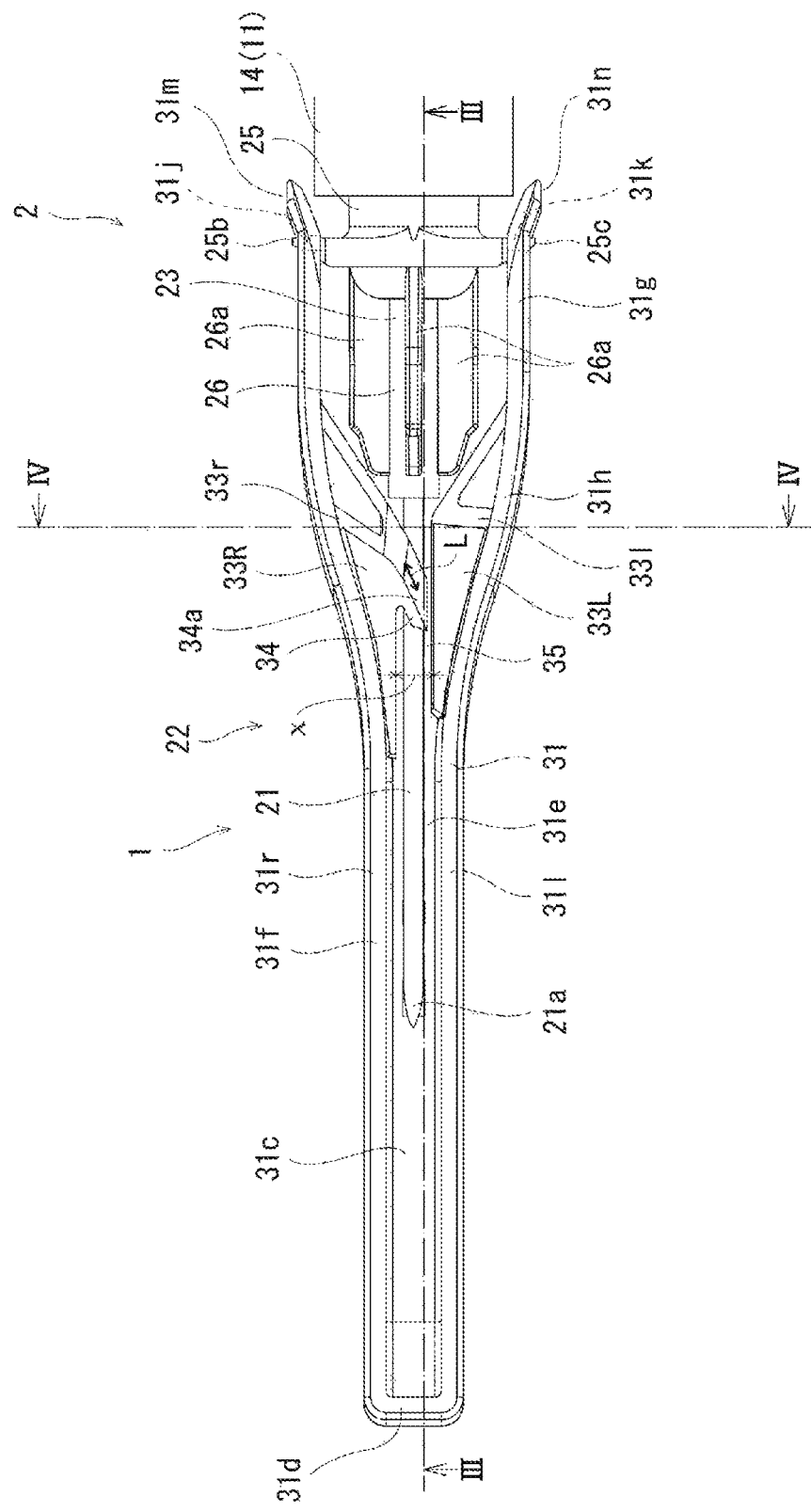
FIG. 2 is an enlarged front view of a needle assembly provided in the needle device of FIG. 1.

The needle device 2 of the embodiment shown in FIG. 1 is mainly used when administering an infusion (for example, a drug solution and a nutrient) to a patient or collecting blood or the like from a patient. The needle device 2 is formed along a predetermined axis L1 and extends in the needle axial direction along the axis L1. The needle device 2 is a so-called needle assembly with a syringe, and includes a syringe 3 and a needle assembly 1 as shown in FIG. 2.

The syringe 3, which is an example of a liquid transfer device, is a device for storing infusion, blood, and the like, and includes a cylinder 11 and a plunger 12. The cylinder 11 is formed in a substantially cylindrical shape and extends in the needle axial direction. The cylinder 11 has an inlet/outlet portion 13 (see FIG. 3) at its distal end, and the inlet/outlet portion 13 is formed smaller in diameter than the remaining portion of the cylinder 11. Further, the inlet/outlet portion 13 is formed substantially in a truncated cone shape, and the outer peripheral portion is formed in a tapered shape which is tapered toward the distal end. The inlet/outlet portion 13 configured in this way has an opening at the distal end, and the inside of the syringe 3 is connected with the outside by this opening. That is, the cylinder 11 is adapted to be able to pour out the infusion therein from the opening and to inject blood or the like into the cylinder 11 from the opening.

The cylinder 11 also has an opening at its proximal end, and the plunger 12 is inserted into the cylinder 11 from this opening. The plunger 12 has a gasket (not shown) on the outer peripheral surface of its distal portion, and the gasket is fitted to the cylinder 11 slidably in the needle axial direction. Further, the plunger 12 has a proximal end projecting from the cylinder 11 so that the user can grip and push the proximal end of the plunger.

The syringe 3 configured in this way can deliver the infusion in the cylinder 11 from the opening of the inlet/outlet portion 13 by pushing the plunger 12 distally, and can draw blood or the like into the cylinder 11 from the opening of the inlet/outlet portion 13 by pulling the plunger 12. Furthermore, the syringe 3 is configured so that the needle assembly 1 can be attached, and the infusion pushed out from the inlet/outlet portion 13 through the needle assembly 1 can be administered to the blood vessel of the patient or the patient's blood is collected through the needle assembly 1. Hereinafter, in order to attach the needle assembly 1 to the syringe 3, the configuration of the syringe 3 will be described in detail.

Figure 3:
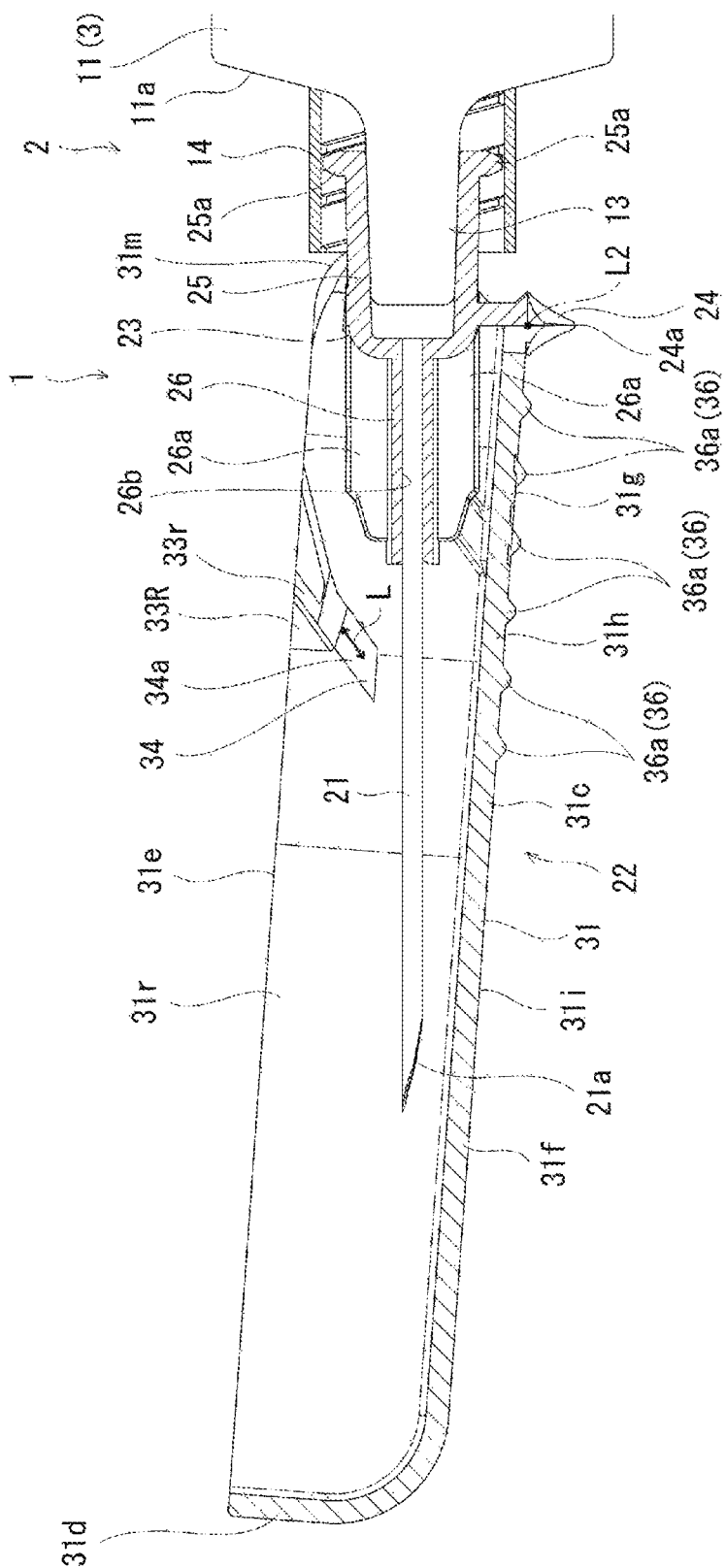
FIG. 3 is an enlarged cross-sectional view of the needle assembly of FIG. 2 taken along cutting line III-III.

As shown in FIG. 3, the cylinder 11 of the syringe 3 has a mounting portion 14 at the distal end thereof and around the inlet/outlet portion 13. The mounting portion 14 has a substantially cylindrical shape, and is formed on a tapered portion 11a between the inlet/outlet portion 13 of the cylinder 11 and the remaining portion. Further, the mounting portion 14 encircles the proximal end portion of the inlet/outlet portion 13 from the radially outer side across the entire circumferential direction, and is disposed having a gap from the inlet/outlet portion 13. Here, the inlet/outlet portion 13 is formed to be longer than the mounting portion 14, and the distal end portion thereof distally projects from the mounting portion 14. Furthermore, a female screw is formed on the inner peripheral surface of the mounting portion 14, and the needle assembly 1 is screwed into the female screw.

<Needle Assembly>

The needle assembly 1 is provided with a needle 21 and a protector 22 as shown in FIG. 1, and the needle 21 punctures the skin, blood vessels, etc. of the patient to administer infusion, or collect blood or the like through the needle 21. In addition, the needle assembly 1 protects the needle 21 by covering the needle 21 with the protector 22 after use, and it is possible to stop the user, the patient, the waste disposal person, etc. from getting stuck or touched with the needle to which blood etc. adheres. The needle assembly 1 having such a function includes the needle 21 and the protector 22 as described above, and a needle hub 23.

[Needle Hub and Needle]

The needle hub 23 shown in FIGS. 2 and 3 is a substantially cylindrical member made of synthetic resin. The needle hub 23 has a large diameter portion 25 at the proximal end and a small diameter portion 26 at the distal end. The large diameter portion 25 is formed to have a larger diameter than the small diameter portion 26, and the inlet/outlet portion 13 of the cylinder 11 can be fitted therein. The large diameter portion 25 is configured to be insertable into the mounting portion 14, and a pair of projection pieces 25a and 25a is formed on the outer peripheral surface of the large diameter portion 25 at the proximal end thereof. The projection pieces 25a are disposed at equal intervals (that is, at intervals of about 180 degrees) in the circumferential direction on the outer peripheral surface, and project outward in the radial direction. The projection pieces 25a can be screwed into a female screw on the inner peripheral surface of the mounting portion 14 in a state where the inlet/outlet portion 13 is inserted into the large diameter portion 25, and the large diameter portion 25 is attached to the distal end of the syringe 3 by the pair of projection pieces 25a and 25a. In addition, the small diameter portion 26 is integrally provided at the distal portion of the large diameter portion 25.

The small diameter portion 26 is formed substantially in a cylindrical shape, and four ribs 26a are integrally formed on the outer peripheral surface thereof. The four ribs 26a are plate-like portions that project radially and extend in the needle axial direction, and are disposed at equal intervals (that is, at intervals of about 90 degrees) in the circumferential direction. Further, the small diameter portion 26 has an inner hole 26b connected to the inside of the large diameter portion 25, and the needle 21 is fitted and fixed to the inner hole 26b.

The needle 21 is a substantially cylindrical hollow needle made of, for example, a metal material or a hard synthetic resin, and extends straight from the needle hub 23 along the axis L1. The needle 21 has its proximal end portion inserted into the needle hub 23 and is fixed to the needle hub 23 by an adhesive or the like, and the remaining portion projects from the needle hub 23 along the axis L1 (that is, one needle axial direction). Further, the needle 21 has a sharp needle tip 21a at the distal end, and the needle tip 21a is sharpened so as to puncture the skin and blood vessels of the patient. Furthermore, the needle hub 23 is provided with the protector 22 in order to protect the needle tip 21a after puncturing and removal, that is, after use.

Protector

The protector 22 is provided pivotably on the needle hub 23 and is configured to be displaced relative to the needle 21 by pivoting. In addition, when the protector 22 is relatively displaced to be directed to the needle 21, the needle 21 can be covered with the protector 22. By being covered, the needle tip 21a of the needle 21 is protected. The protector 22 having such a function has a protector main body 31, a pair of guide ribs 33L and 33R, and a claw-like portion 34.

Figure 4:
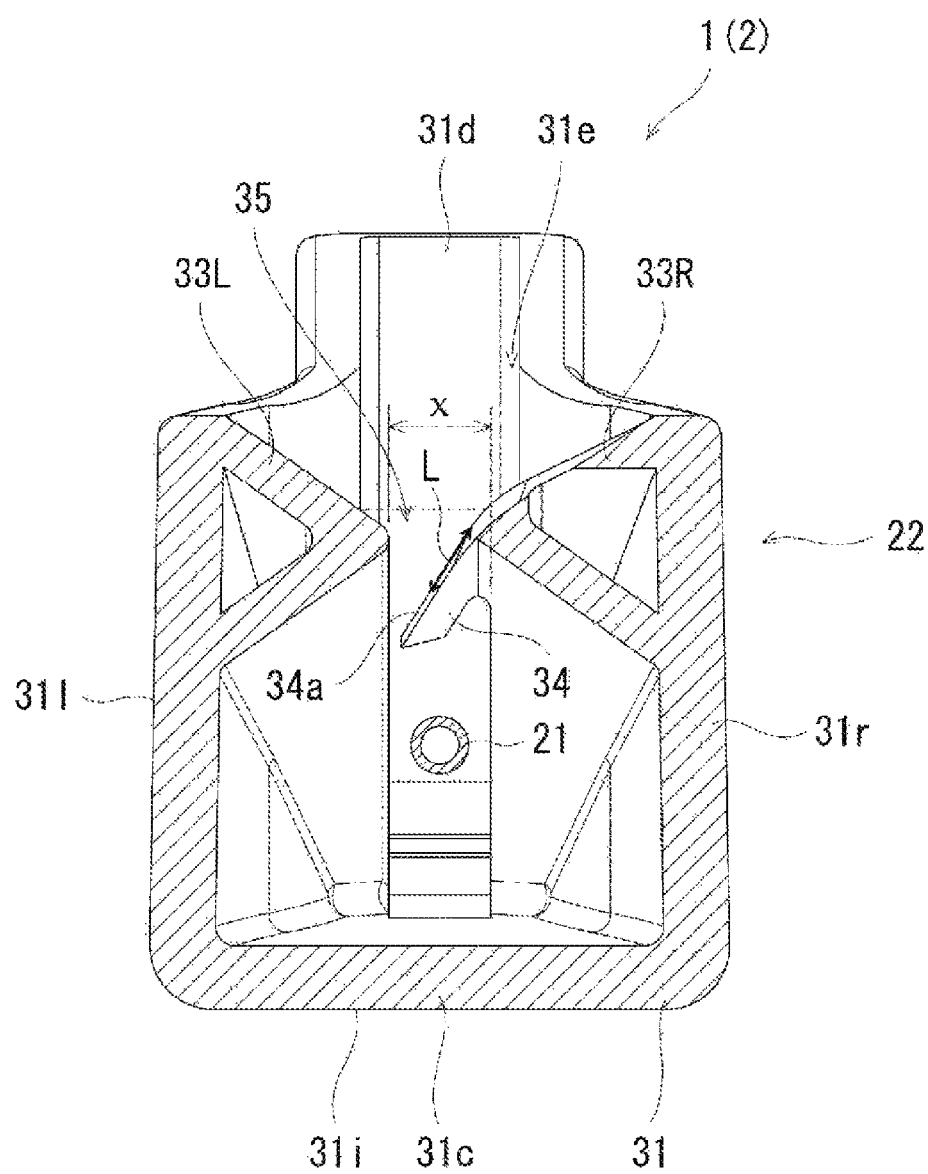
FIG. 4 is an enlarged cross-sectional view of the needle assembly of FIG. 2 taken along cutting line IV-IV.

The protector main body 31 is a member longer than the needle 21, and a cross section cut at a plane orthogonal to the longitudinal direction is formed substantially in a U shape as shown in FIG. 4. That is, the protector main body 31 has a pair of side face portions 31l and 31r, a back face portion 31c, and a ceiling portion 31d. The pair of side face portions 31l and 31r is formed to be longer than the needle 21 and disposed to face each other on both sides in the width direction orthogonal to the longitudinal direction. Further, the pair of side face portions 31l and 31r is provided with the back face portion 31c which bridges the side face portions 31l and 31r at the one side in the depth direction which is orthogonal to the longitudinal direction and the width direction, that is, at depth side end. That is, the protector main body 31 has a pair of side face portions 31l and 31r and a back face portion 31c in three directions orthogonal to the longitudinal direction. Moreover, the ceiling portion 31d is provided in the distal portion of the three face parts 31c, 31l, 31r, and has covered the space in the protector main body 31 at the one side in the longitudinal direction. That is, the ceiling portion 31d is provided on the pair of side face portions 31l and 31r so as to close the entire one side in the longitudinal direction.

The protector main body 31 configured in this way has an opening in two directions, that is, on the other side in the depth direction (that is, the near side and the remaining one direction in the directions orthogonal to the longitudinal direction) and on the other side in the longitudinal direction, and an opening 31e on the other side in the depth direction (that is, the opposite side of the back face portion 31c) is formed to conform to the shapes of the needle 21 and the needle hub 23. The opening 31e does not have to perfectly conform to the shapes of the needle 21 and the needle hub 23, and the width of the opening 31e may be larger than the diameters of the needle 21 and the needle hub 23. Further, the opening on the other side in the longitudinal direction is formed so that the needle hub 23 can be housed therein. The protector main body 31 configured in this way can receive the needle 21 and the needle hub 23 into the protector main body 31 from the opening 31e by pivoting the protector 22, and the needle hub 23 is disposed in the opening on the other side in the longitudinal direction when disposed into the protector main body 31. Further, in order to pivot the protector 22, a hinge 24 is bridged between the protector main body 31 and the needle hub 23.

Figure 5:
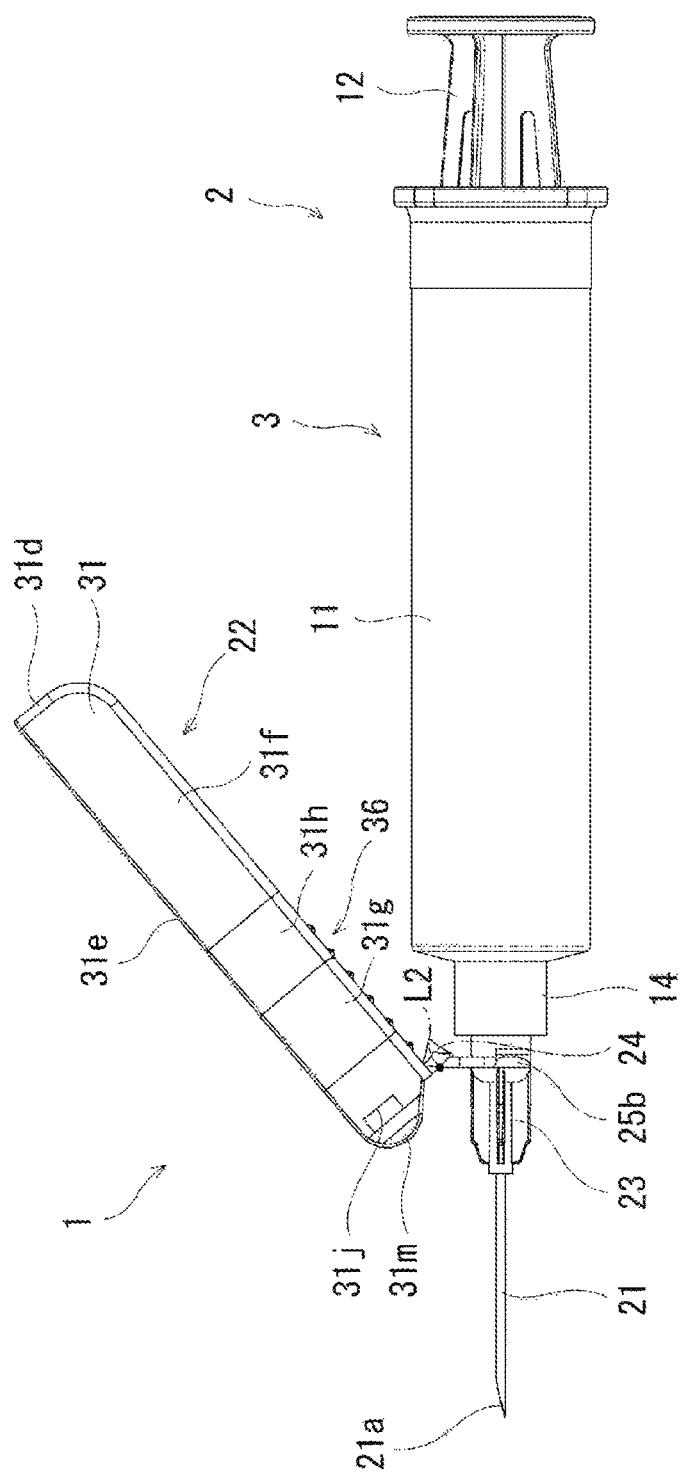
FIG. 5 is a view of the needle device of FIG. 1 in use when using the needle device.
Figure 7:
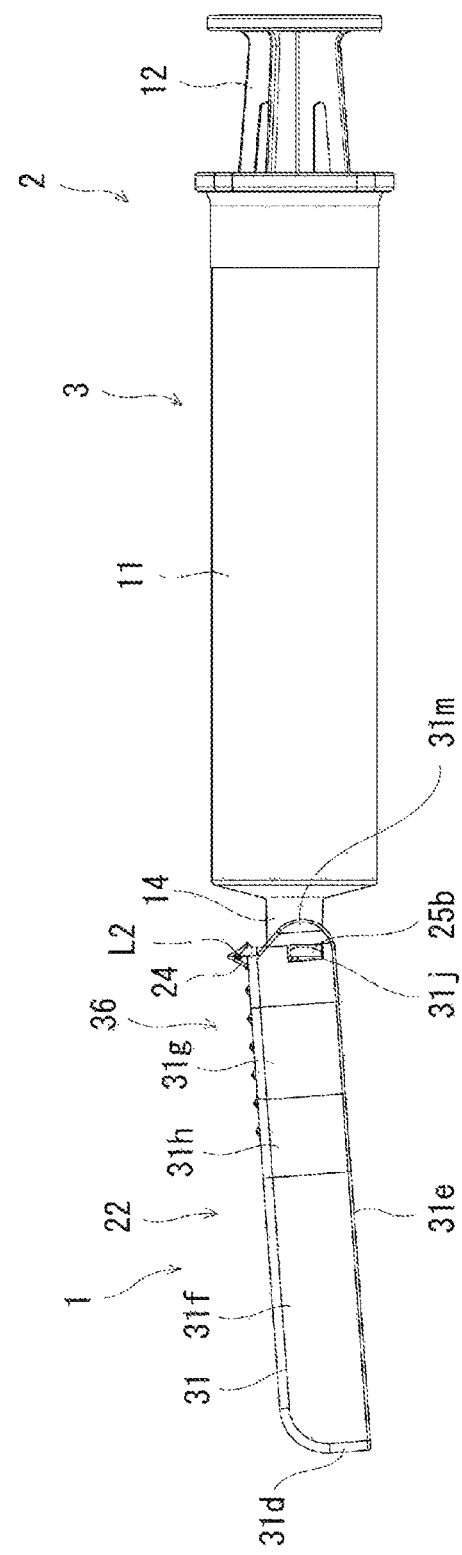
FIG. 7 is a view of the needle device of FIG. 1 in a protected state in which the needle tip is protected.

The hinge 24 is formed in a plate shape, and is integrally provided on the large diameter portion 25 of the needle hub 23 so as to project radially outward. Further, the tip end of the hinge 24 is provided at the other end of the back face portion 31c in the longitudinal direction. Thus, the hinge 24 is provided so as to bridge the large diameter portion 25 of the needle hub 23 and the protector main body 31. Furthermore, the hinge 24 can be folded back at its middle portion 24a, while being able to open up to a predetermined angle α (for example, 120 degrees or more). Thereby, the protector main body 31 can be pivoted around a pivot L2 extending in the width direction of the protector main body 31 in the vicinity of the middle portion 24a. By being configured to be pivotable in this manner, the protector main body 31 (that is, the protector 22) is directed to the needle 21 from the use position where the hinge 24 is open (see FIG. 5), and further can be relatively displaced to the protection position where the hinge 24 is closed (see FIG. 7). In addition, the use position which is an example of a non-protection position is a position where the protector main body 31 is disposed such that the needle tip 21a is exposed in the case of a puncturing operation, and in the use position, the one side portion in the longitudinal direction of the protector main body 31 is directed to the other side in the needle axial direction, and the protector main body 31 is placed away from the needle 21. Further, the protection position is a position where the protector main body 31 is disposed to protect the needle tip 21a after the puncturing operation, and the protector main body 31 covers the needle 21 in the protection position. Therefore, the protector main body 31 exposes the needle tip 21a therefrom at the time of the puncturing operation, and covers the needle 21 to protect the needle tip 21a after the puncturing operation is completed.

In the protection position, as shown in FIG. 2, not only the needle tip 21a but also the needle hub 23 is housed in the protector main body 31. That is, the protector main body 31 is formed to conform to the shapes of the needle 21 and the needle hub 23 as described above, and the other side portion in the longitudinal direction (i.e., a hub housing portion 31g) is formed wide, as compared to the one side portion in the longitudinal direction (that is, a needle tip housing portion 31f). A guide portion 31h is formed between the needle tip housing portion 31f and the hub housing portion 31g, and the width of the guide portion 31h gradually narrows toward the one side of the longitudinal direction. The guide ribs 33L and 33R are respectively provided on the inner side face of the pair of side face portions 31l and 31r in the guide portion 31h formed in this manner.

The pair of guide ribs 33L and 33R is provided so as to project radially inward from the side face portions 31l and 31r. Further, the pair of guide ribs 33L and 33R obliquely extends toward one side of the depth direction and the one side of the longitudinal direction with a certain distance x in the width direction, and an insertion groove 35 is formed therebetween. The insertion groove 35 obliquely extends in the one side in the depth direction and the one side in the axial direction, and extends along the center line of the protector main body 31 in a front view. The needle tip housing portion 31f also extends along the center line, and the insertion groove 35 and the inside of the needle tip housing portion 31f are straightly connected to each other. Thereby, when the protector main body 31 is pivoted to the protection position, the needle 21 is housed in the insertion groove 35 and the needle tip housing portion 31f. Further, the pair of guide ribs 33L and 33R forms guide faces 33l and 33r on the other side in the depth direction, that is, on the near side. The guide faces 33l and 33r are formed substantially in a triangular shape in a front view, and has an end edge on the other side in the longitudinal direction, the end edge being inclined toward the inward side in the width direction and to the one side in the longitudinal direction. As a result, it is possible to widen a space between the other side end portions in the longitudinal direction of the pair of guide ribs 33L and 33R and to house the distal end portion of the needle hub 23 therebetween. Therefore, the length of the protector main body 31 can be shorter than that of the prior art. In addition, the guide faces 33l and 33r are inclined toward the inward side in the width direction and the one side in the depth direction, that is, the depth side. Therefore, the needle 21 is guided toward the insertion groove 35 by pressing the needle 21 against the guide faces 33l and 33r. One of the pair of guide ribs 33L and 33R configured in this manner, that is, the one guide rib 33R in the present embodiment, is provided with the claw-like portion 34.

The claw-like portion 34 is a strip-like plate, and is integrally provided on the one guide rib 33R. More specifically, the claw-like portion 34 projects from the one guide rib 33R toward the other guide rib 33L (that is, inward of the width direction) so as to extend the guide face 33r of the one guide rib 33R. Thus, the claw-like portion 34 is disposed to cross the insertion groove 35 in the width direction in a front view. Therefore, the claw-like portion 34 is disposed on the track of the needle 21 when the protector main body 31 is relatively pivoted to house the needle 21, so that the needle 21 comes into contact with the claw-like portion 34. Further, the claw-like portion 34 is like a cantilever whose tip end is free, and is bent to the depth side by pushing the claw-like portion 34 with the needle 21 with the base end of the claw-like portion 34 as a fulcrum. As a result, the insertion groove 35 closed by the claw-like portion 34 can be opened and the needle 21 can be inserted into the insertion groove 35. That is, the needle 21 is permitted to proceed to the protection position in the protector main body 31.

Further, the claw-like portion 34 is inclined so as to extend to the depth side as being closer to the inward side in the width direction. This makes it possible to reduce the amount by which the claw-like portion 34 is bent to the depth side as compared to the case where the claw-like portion 34 is not inclined to the depth side, and the needle 21 can be guided into the insertion groove 35 by the near side face 34a of the claw-like portion 34. Further, the claw-like portion 34 is inclined so as to extend to the one side in the longitudinal direction as being closer to the inward side in the width direction. As a result, it is possible to shift the contact point where the claw-like portion 34 contacts the needle 21 to the one side in the longitudinal direction with respect to the base end of the claw-like portion 34. As a result, the linear distance L connecting linearly the base end of the claw-like portion 34 and the contact point can be increased, compared to the case where the claw-like portion 34 does not extend in the longitudinal direction (that is, when the claw-like portion 34 simply extends in the width direction). The linear distance L corresponds to the distance between the fulcrum (base end of the claw-like portion 34) and the force point (contact point), and the force necessary to cause the claw-like portion 34 to bend is determined according to the linear distance L. Therefore, it is preferable to increase the linear distance L. When the claw-like portion 34 simply extends in the width direction, it is necessary to widen the insertion groove 35 in order to increase the linear distance L. On the other hand, the contact point can be shifted to the one side in the longitudinal direction by inclining the claw-like portion 34 so as to extend to the one side in the longitudinal direction, so that the linear distance L can be made to be long without widening the insertion groove 35. As a result, the portion of the opening 31e into which the needle 21 is inserted and the width of the insertion groove 35 can be narrowed, and the protector main body 31 can be miniaturized. When the length in the width direction of the claw-like portion 34 is not changed, the load at the time of bending the claw-like portion 34 can be reduced, and the operability when covering the needle 21 with the protector main body 31 is improved. Therefore, the protector main body can be easily moved to the protection position.

In addition, the claw-like portion 34 has the following function by being inclined so as to extend to one side in the longitudinal direction as being closer to the inward side in the width direction. That is, the needle 21 also has flexibility, and is bent to the near side by being pressed against the claw-like portion 34. The amount of bending of the needle 21 varies depending on the load acting on the needle and the position at which the load acts. The closer the position is to the proximal end, the shorter the distance between the fulcrum and the force point, and the smaller the amount of bending. On the other hand, by setting the contact point to the proximal end of the needle 21, the load absorbed by bending is reduced, and the load is transmitted to the claw-like portion 34 more efficiently than that in the case of setting the contact point to the distal end. Therefore, even if the pressing load acting on the needle 21 is the same, by setting the contact point to the proximal end of the needle 21, the claw-like portion 34 is bent more largely than that in the case of setting the contact point to the distal end of the needle. That is, when the claw-like portion 34 is inclined, the contact point to the needle 21 can be positioned at the proximal end of the needle 21, as compared with the case where the claw-like portion 34 extends straight inward in the width direction. By setting the contact point to the proximal side of the needle 21, the claw-like portion 34 can be bent with a smaller pressing load than that in the case of setting the contact point to the distal side.

Further, in the needle assembly 1, when the claw-like portion 34 is pushed to open, the claw-like portion 34 first comes into contact with the needle 21 at the base end, and the contact point is shifted to the tip end as the needle 21 is pushed in. Therefore, although immediately after contact, the largest load is required to bend the claw-like portion 34, since the contact point immediately after contact is brought closer to the proximal end of the needle 21, the load can be efficiently transmitted from the needle 21 to the claw-like portion 34 immediately after contact. Thus, the claw-like portion 34 can be bent and pushed with a smaller force to open.

Furthermore, the claw-like portion 34 is formed in a plate shape and has an elastic restoring force. That is, after the claw-like portion 34 is pushed to open, the needle 21 enters the depth side by the claw-like portion 34 (that is, the protector main body 31 moves to the protection position). Thus, the claw-like portion 34 returns to the original position (that is, the initial position), and is disposed to cross the insertion groove 35. Thereby, the needle 21 in the insertion groove 35 is locked by the claw-like portion 34 when it is going to be detached, and detachment of the needle 21 from the opening 31e of the protector main body 31 is suppressed. In this way, the needle 21 is held in the protector main body 31 in a state where the needle 21 is covered with the protector main body 31 and the needle tip 21a is protected. Moreover, the protector main body 31 covers the needle 21 with the back face portion 31c which covers the needle 21 at the depth side, and a non-slip part 36 as shown in FIG. 3 is formed on the back face portion 31c.

The non-slip part 36 is formed on the back face portion 31c of the protector main body 31 and on the back face 31i on the outside thereof, on which the user's thumb, forefinger or the like can be placed. More specifically, the non-slip part 36 is formed on the back face 31i and is formed at the hub housing portion 31g and the guide portion 31h. The non-slip part 36 has a plurality of ridges 36a, for example, six ridges 36a. In addition, the number of ridges 36a is not limited to six, may be five or less, and may be seven or more. The six ridges 36a project in the depth direction from the back face and extend in the width direction, and are disposed at equal intervals in the longitudinal direction. In the non-slip part 36 configured in this manner, the user's thumb or forefinger placed thereon is caught by the plurality of ridges 36a, and the user's thumb or forefinger or the like with respect to the protector main body 31 does not slip. As a result, the user's thumb, forefinger, or the like can be placed on the non-slip part 36 of the protector main body 31, and the protector main body 31 can be pushed toward the needle 21 by the placed finger. On the back face 31i, the non-slip part 36 is formed on the other side in the longitudinal direction, while there is a portion in which the non-slip part 36 is not formed on the one side in the longitudinal direction. Various things (a stand, a tray, etc.) can be pushed to the one side portion in the longitudinal direction, and the protector main body 31 can be pivoted toward the needle 21 by the pushing.

Furthermore, in the protector main body 31, the one side portion in the longitudinal direction of the back face 31i, specifically, the entire needle tip housing portion 31f of the back face 31i is formed to be smooth. Therefore, since the area of the portion against which an object is pushed can be larger than that of the prior art, it is easy to push various objects against the entire needle tip housing portion 31f. Therefore, the operability at the time of covering the needle 21 with the protector main body 31 can be improved, and it is easy to move the protector main body 31 to a protection position. In addition, since the entire needle tip housing portion 31f of the back face 31i is formed to be smooth, the portion against which various objects are pushed is secured in a wide range, making it possible to perform an easy push. Furthermore, the one side portion in the longitudinal direction of the back face portion 31c is round-chamfered and is curved to be connected to the ceiling portion 31d, and it is possible to pivot the protector main body 31 by various things pushed against this portion. In the protector main body 31 configured as described above, the back face portion 31c is formed substantially flat, and the thickness in the depth direction can be suppressed. Thus, the protector 22 can be stopped from interfering with the puncturing operation at the time of puncturing.

Moreover, the protector main body 31 has flare portions 31m and 31n at the other side end in the longitudinal direction of a pair of side face portions 31l and 31r. The flare portions 31m and 31n are inclined so as to be away from each other as being closer to the other side in the longitudinal direction as shown in FIG. 2, and have a flare shape. Further, engagement holes 31j and 31k are respectively formed in the flare portions 31m and 31n, and the engagement holes 31j and 31k penetrate the other side end in the longitudinal direction of the pair of side face portions 31l and 31r in the width direction. Furthermore, the large diameter portion 25 of the needle hub 23 is provided with a pair of engagement pieces 25b and 25c which correspond to the pair of engagement holes 31j and 31k. More specifically, the pair of engagement pieces 25b and 25c is provided at the position same as the position of the hinge 24 in the needle axial direction in the large diameter portion 25, and projects from the large diameter portion 25 in one and the other directions orthogonal to the extending direction of the hinge 24.

Figure 6:
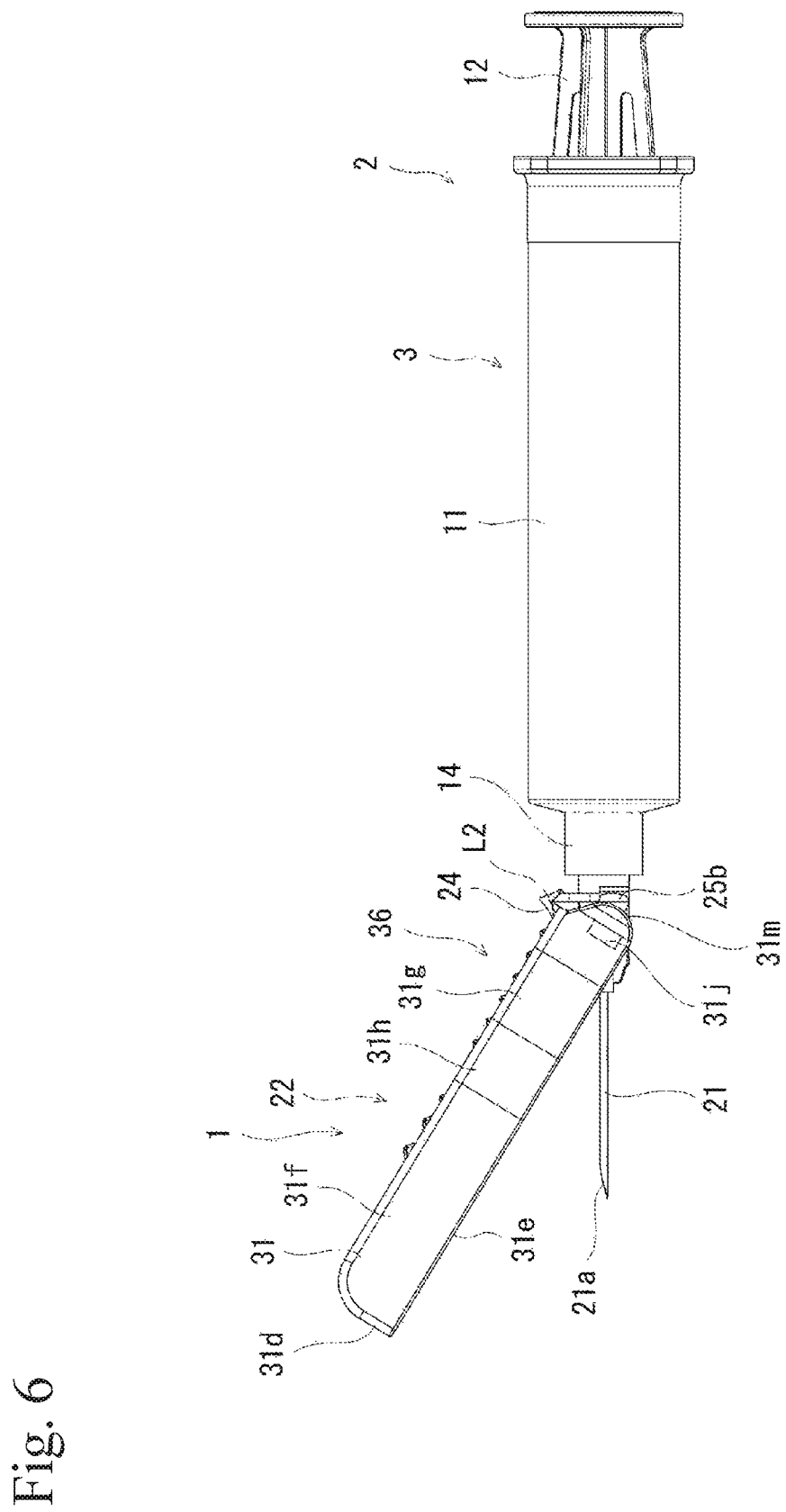
FIG. 6 is a view of the needle device of FIG. 1, showing the state in which a needle tip is moved toward the protection position.

The pair of engagement pieces 25b and 25c disposed in this manner is adapted to come into contact with the flare portions 31m and 31n when the protector main body 31 is pivoted, and the pivot of the protector main body 31 is restricted by a pair of flare portions 31m and 31n when the engagement pieces come into contact with the flare portions (see FIG. 6). On the other hand, the pair of flare portions 31m and 31n is formed so as to bend outward in the width direction with respect to the remaining portion of the pair of side face portions 31l and 31r. Therefore, when the pair of engagement pieces 25b and 25c is pushed against the pair of flare portions 31m and 31n so as to further pivot the protector main body 31, the pair of flare portions 31m and 31n is widened outward. As a result, the pair of engagement pieces 25b and 25c is inserted between the flare portions to further pivot the protector main body 31. When the protector main body 31 is pivoted as it is, the protector main body 31 is eventually pivoted and moved to the protection position, the engagement pieces 25b and 25c fit into the respective engagement holes 31j and 31k. Accordingly, the protector main body 31 is held in a protection position. The outer dimension of the engagement holes 31j and 31k are formed larger than the outer dimension of the engagement pieces 25b and 25c in order to facilitate the fitting. Therefore, the protector main body 31 can be slightly pivoted relative to the needle hub 23 even after being fitted.

<Needle Tip Protection by Needle Assembly>

The needle assembly 1 configured in this way constitutes the needle device 2 together with the syringe 3 by attaching the needle hub 23 to the syringe 3, and can administer the infusion in the syringe 3 to the patient via the needle 21 or can collect blood from the patient to store the blood in the syringe 3. At the time of administration of the infusion or blood collection, the protector main body 31 is folded back so as to be detached from the needle (that is, toward the syringe 3) and relatively pivoted to the use position, and the protector 22 does not disturb the puncturing operation (see, for example, FIG. 5). Then, the user holds the cylinder 11 with one hand and pushes the protector main body 31 against the cylinder 11 with any finger (for example, a thumb or forefinger) of the one hand holding the cylinder 11 so that the protector main body 31 does not head toward the needle 21. The needle device 2 is punctured into a blood vessel or the like of the patient after being in such a use state. After the puncture, depending on the purpose, the plunger 12 is pushed to administer the infusion, or the plunger 12 is pulled to collect blood. When administration of infusion or blood collection is completed, the needle tip 21a is removed from the blood vessel or the like.

When the user removes the needle 21, the user pivots the protector main body 31 toward the needle 21 to protect the needle tip 21a. Specifically, the user pushes the non-slip part 36 with a finger or pushes the back face 31i (for example, one end in the longitudinal direction of the back face 31i) against an object to pivot the protector main body 31. When the protector main body 31 in the use position is pivoted toward the needle 21, the flare portions 31m and 31n of the protector main body 31 contact the engagement pieces 25b and 25c, and the pivot of the protector main body 31 is restricted (see FIG. 6). When the protector main body 31 is kept pushed to keep pivoting further, the pair of flare portions 31m and 31n is widened outward in the width direction by the engagement pieces 25b and 25c so as to be able to separate from each other, and eventually the engagement pieces 25b and 25c enters a pair of flare portions 31m and 31n. As a result, the restriction on the pivot of the protector main body 31 is released, and the protector main body 31 can be further pivoted.

When the protector main body 31 is further pivoted, the needle 21 eventually comes into contact with one of the guide faces 33l and 33r (for example, the guide face 33r). When the protector main body 31 is further pivoted, the needle 21 proceeds to the depth side of the protector main body 31 while being guided toward the insertion groove 35 by the guide face 33r, and eventually comes into contact with the claw-like portion 34. In addition, also when the needle 21 comes into contact with the other guide face 33l, the needle 21 proceeds to the depth side of the protector main body 31 while being guided toward the insertion groove 35 by the guide face 33l. When the needle 21 reaches the insertion groove 35, the needle 21 comes into contact with the claw-like portion 34. In addition, the needle 21 may directly reach the insertion groove 35 without contacting any of the guide faces 33l and 33r, and in this case, the needle 21 contacts the claw-like portion 34 without being guided by the guide faces 33l and 33r.

When the protector main body 31 is further pushed from the state in which the needle 21 comes into contact with the claw-like portion 34, the claw-like portion 34 is pushed by the needle 21 and is bent to the depth side. As a result, the insertion groove 35 is gradually opened, and the insertion groove 35 is opened to such an extent that the needle 21 can pass through eventually. Furthermore, by pushing the protector main body 31 to the protection position, the needle 21 passes through the lateral side of the claw-like portion 34 and enters the depth side of the insertion groove 35, and the needle 21 is housed in the insertion groove 35. Thus, the needle 21 is covered with the protector main body 31 and the needle tip 21a of the needle 21 is protected by the protector main body 31. In addition, although the claw-like portion 34 of this embodiment has a clearance gap with the guide rib 33L at the initial position, the tip end thereof may contact the guide rib 33L.

On the other hand, when the needle 21 is housed in the insertion groove 35, the claw-like portion 34 elastically restores and returns to the initial position, and the insertion groove 35 is closed again by the claw-like portion 34. As a result, the needle 21 in the insertion groove 35 is stopped from being detached from the opening 31e of the protector main body 31. That is, the needle 21 is held in the protector main body 31 in a state where the needle 21 is covered with the protector main body 31 and the needle tip 21a is protected. Further, by pivoting the protector main body 31 to the protection position, the pair of engagement holes 31j and 31k of the protector main body 31 is engaged with the corresponding engagement pieces 25b and 25c (see FIG. 7). Thus, the protector main body 31 is held in the protection position, and the practitioner can visually determine that the protector main body 31 is in the protection position.

In this manner, the needle tip 21a is protected by the protector main body 31, and the needle device 2 is discarded with the protector main body 31 held at the protection position. As a result, it is possible to stop the needle from being discarded with the contaminated needle tip 21a being exposed, and it is possible to stop a user, a patient, a waste disposer or the like from getting stuck by the needle tip 21a to be infected with bacteria, viruses, etc.

In the needle assembly 1 configured as described above, as described above, when the protector main body 31 is pivoted, the flare portions 31m and 31n first contact the engagement pieces 25b and 25c, and the protector main body 31 is further pushed to be moved to a protection position. Therefore, unless the practitioner moves the protector main body 31 to the protection position with the intention of protecting the needle tip 21a, the protector main body 31 will not easily move to the protection position. Therefore, protection of the needle tip 21a is more reliably performed by the intention of the practitioner.

Further, in the needle assembly 1, when the protector main body 31 is pushed in a state where the flare portions 31m and 31n are in contact with the engagement pieces 25b and 25c, the flare portions 31m and 31n are bent so as to be widened by the engagement pieces 25b and 25c. Further, by pushing the protector main body 31, the engagement pieces 25b and 25c enter the space between the flare portions 31m and 31n, and it is possible to pivot the protector main body 31 to the protection position. Therefore, when pivoting the protector main body 31 to the protection position, it is possible to give the practitioner a feeling that the flare portions 31m and 31n pass over the engagement pieces 25b and 25c. Therefore, it is possible to give the practitioner a feeling that the needle tip 21a is housed in the protector main body 31, and protection of the needle tip 21a is performed more reliably. Thereafter, since the pair of engagement holes 31j and 31k is engaged with the corresponding engagement pieces 25b and 25c, the determination can be made by not only the visual indication that the protector main body 31 is held in the protection position as described above, but also by sounds and responses. As a result, protection of the needle tip 21a is performed more reliably.

Although the flare portions 31m and 31n are formed to be flexible and widened in the outward direction (i.e., flared), they do not have to have such a shape. For example, as long as the other side end in the longitudinal direction of the pair of side face portions 31l and 31r have flexibility even if the other side end has a straight shape, the other side end in the longitudinal direction of the pair of side face portions 31l and 31r is widened by the engagement pieces 25b and 25c, and the other side end can pass over the engagement pieces 25b and 25c to move the protector main body to the protection position. As a result, as with the flare portions 31m and 31n, protection of the needle tip 21a is performed more reliably. Further, the other side end in the longitudinal direction of the pair of side face portions 31l and 31r is not limited to have the flare shape described above, and may have a vane shape or a skirt shape, and any shape may be acceptable as long as it is widened by the engagement pieces 25b and 25c.

Second Embodiment

A needle device 2A of the second embodiment is similar in configuration to the needle device 2 of the first embodiment. Therefore, in the following, regarding the configuration of the needle device 2A of the second embodiment, components different from those of the needle device 2 of the first embodiment will be mainly described. The same reference numerals are given to the same components, and the description is omitted.

Figure 8:
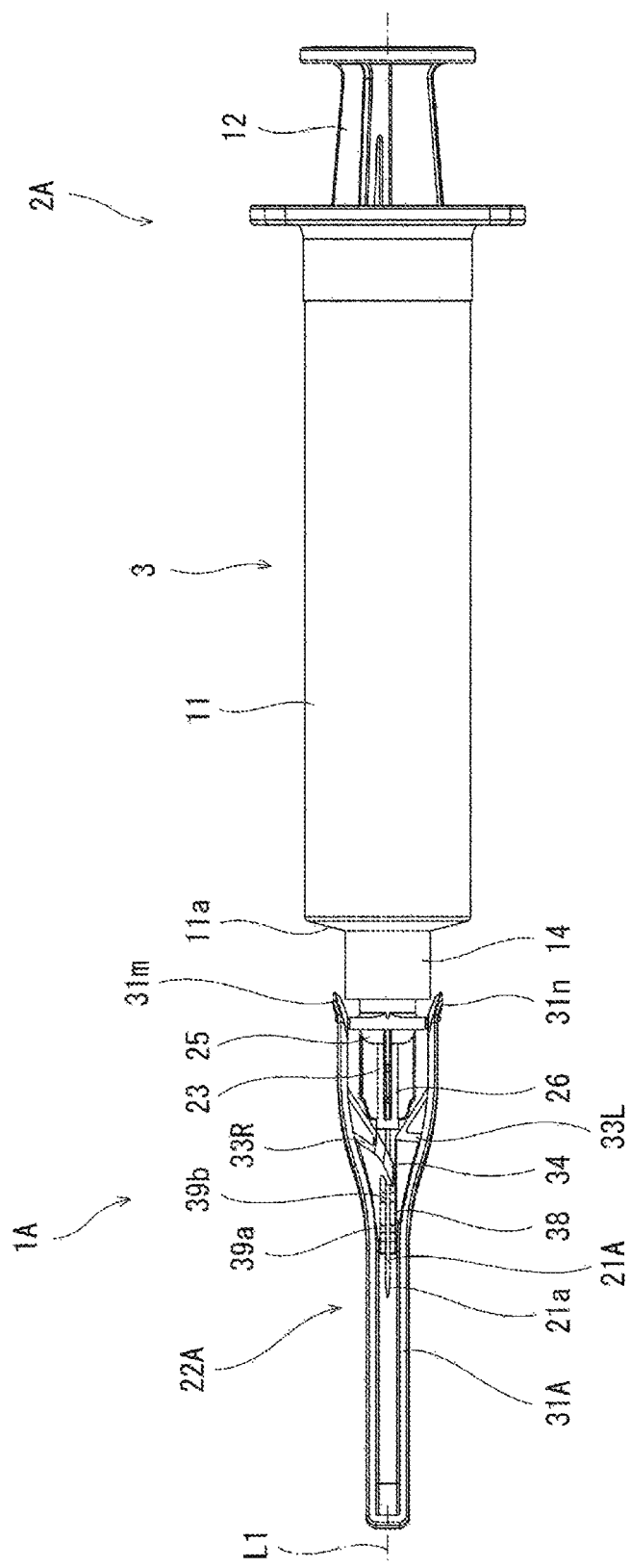
FIG. 8 is a front view of the needle device according to the first embodiment of the present invention as viewed from the side.
Figure 9:
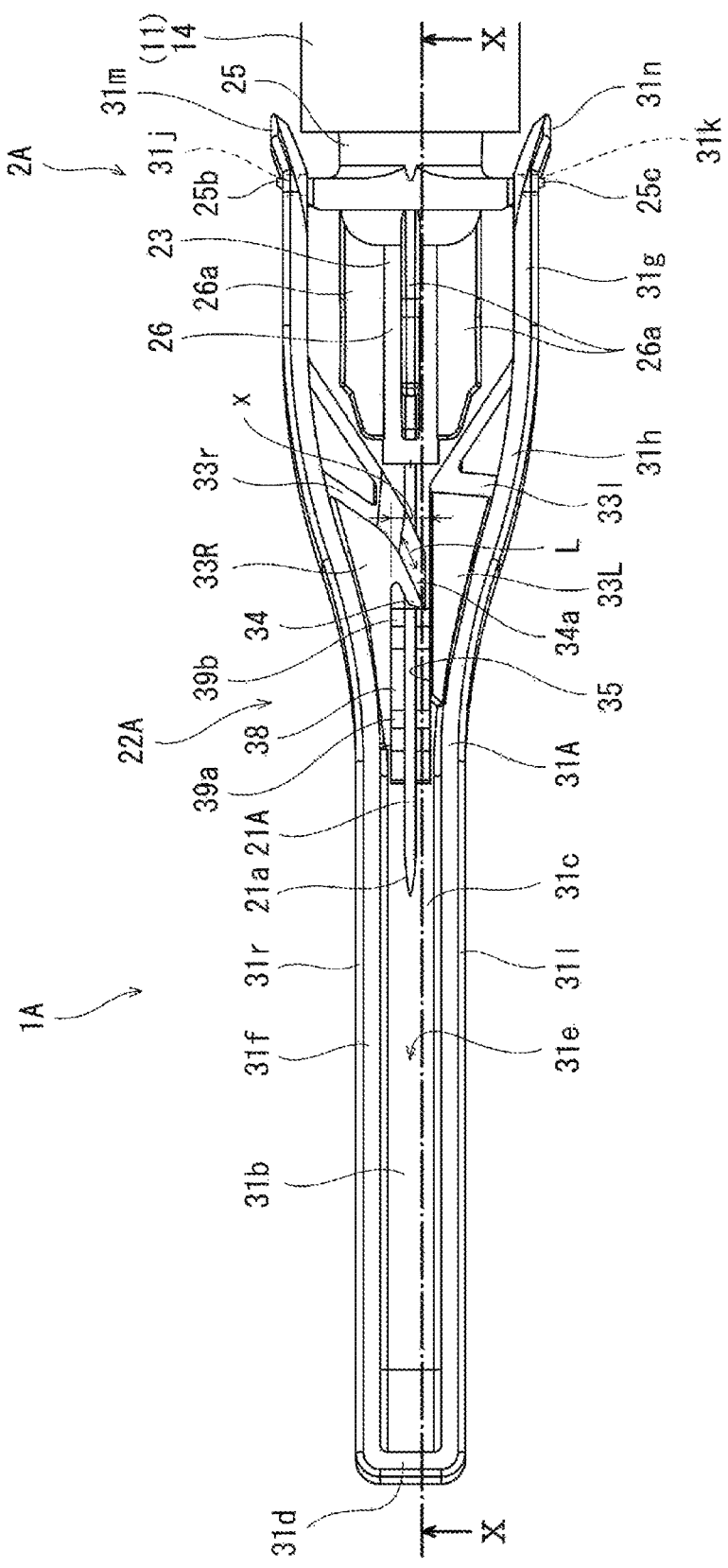
FIG. 9 is an enlarged front view of a needle assembly provided in the needle device of FIG. 8.
Figure 10:
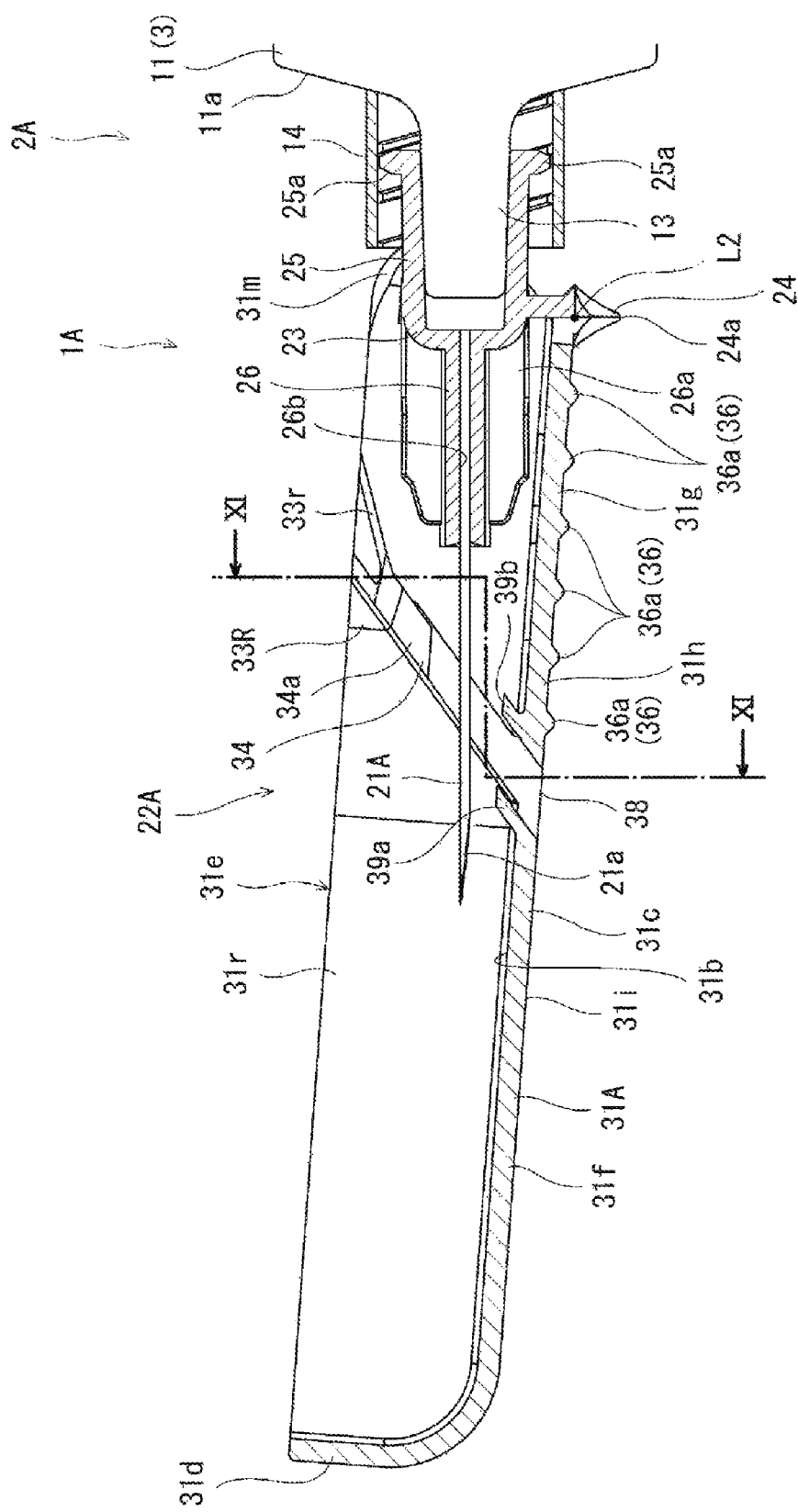
FIG. 10 is an enlarged cross-sectional view of the needle assembly of FIG. 9 taken along cutting line X-X.

A needle assembly 1A of the needle device 2A of the second embodiment includes a needle 21A, a protector 22A, and the needle hub 23 as shown in FIG. 8. The needle 21A is a thin needle 21A having a gauge of 20G or more, and employs a relatively short needle. As shown in FIGS. 9 and 10, the needle tip 21a is located in the vicinity of a window 38 to be described later. A protector main body 31A of a protector 22 is configured as follows.

Figure 11:
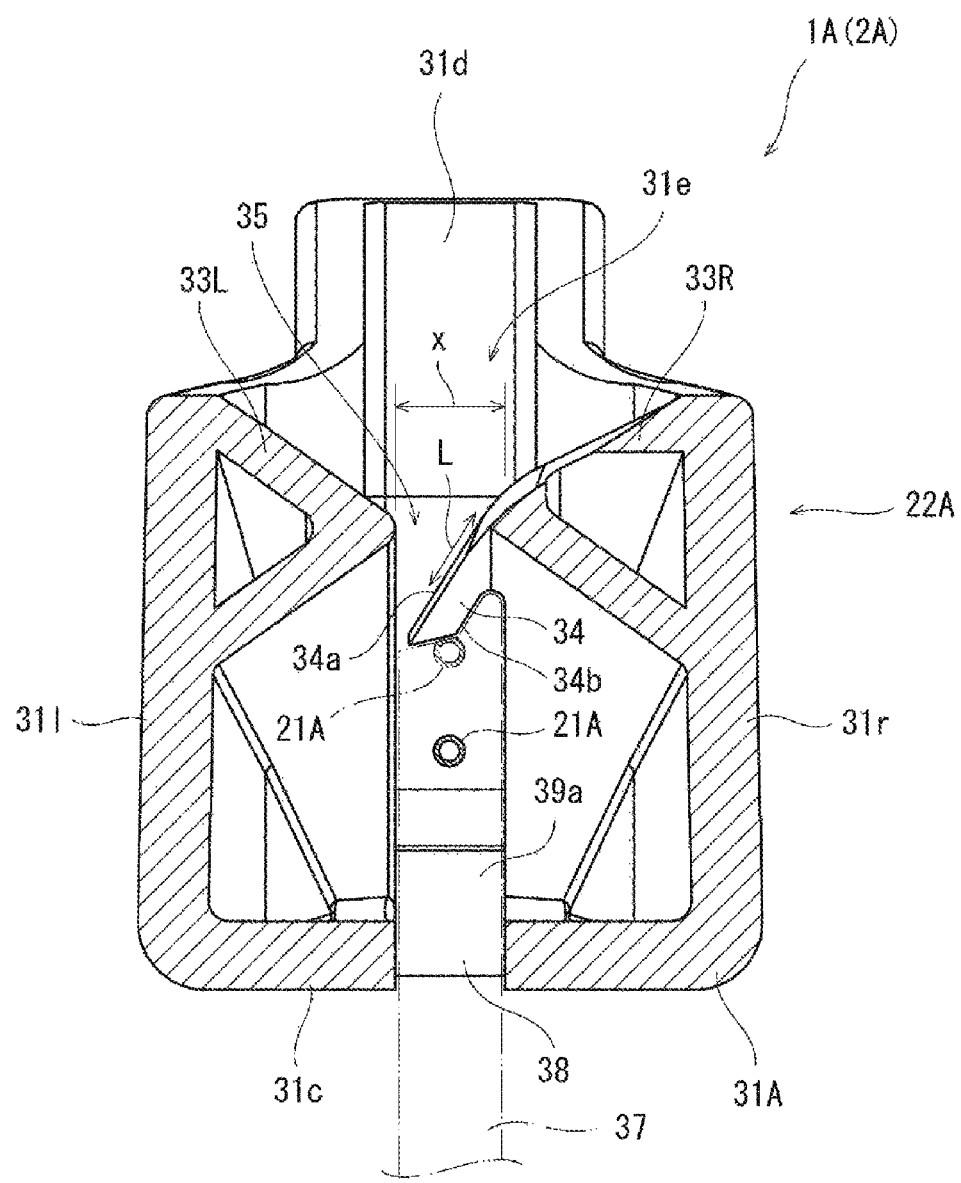
FIG. 11 is an enlarged sectional view of the needle assembly of FIG. 10 taken along cutting line XI-XI.

That is, the protector main body 31A is molded by injection molding, and is molded integrally with the pair of guide ribs 33L and 33R when molded. The claw-like portion 34 is also formed together with the pair of guide ribs 33R. Since the claw-like portion 34 is formed to project from one guide rib 33R, when molded, for example, a molding pin 37 (see FIG. 11) is used. The molding pin 37 is inserted into a mold for injection molding, and forms a depth side face 34b of the claw-like portion 34 by its tip end face as shown in FIG. 11, for example. At this time, the window 38 is formed by the molding pin 37 on the back face portion 31c of the protector main body 31A. The window 38 obliquely penetrates the back face portion 31c so as to be inclined toward the near side as shown in FIG. 10 and the other side in the longitudinal direction, and is formed toward the claw-like portion 34. Thus, the window 38 is formed by the molding pin 37 in injection molding. Therefore, the window 38 is formed near the claw-like portion 34. Further, as in the present embodiment, the window 38 is formed in the vicinity of the needle tip 21a when the needle 21A is short (more specifically, in the case where the needle 21A is short to the degree that the needle tip 21a is positioned at the one side in the longitudinal direction relative to the window 38). Therefore, when the needle 21A is folded or bent, the needle tip 21a can easily enter the window 38. Therefore, the back face portion 31c is integrally provided with a pair of barriers 39a and 39b.

The pair of barriers 39a and 39b is formed on the inner face 31b of the back face portion 31c so as to be adjacent to the one side and the other side in the longitudinal direction of the window 38. Further, the pair of barriers 39a and 39b projects to the near side from the inner face 31b of the back face portion 31c, and the window 38 extends in a penetrating direction in which the back face portion 31c is penetrated. The pair of barriers 39a and 39b formed in this way is formed along the window 38 extending in the penetrating direction, and can be integrally molded with the claw-like portion 34 by the molding pin 37. The pair of barriers 39a and 39b formed in this manner suppresses entry of the needle tip 21a of the needle 21A into the window 38 when an undesired load is applied to the protector 22 as described later. Thus, the pair of barriers 39a and 39b is formed on the inner face 31b of the back face portion 31c.

Figure 12A:
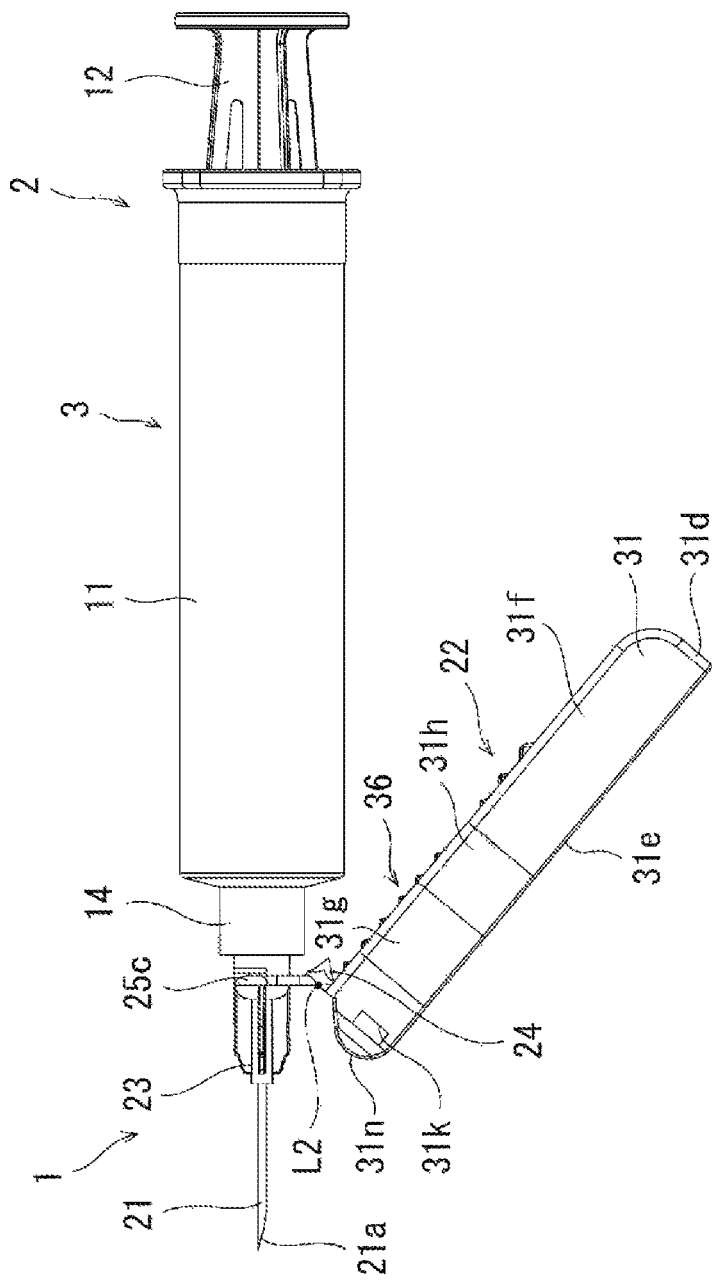
FIG. 12A is a view of the needle device of FIG. 8 in use when using the needle device.

The needle assembly 1A configured in this way is used in the same manner as the needle assembly 1 of the first embodiment. That is, at the time of administration of the infusion or blood collection, the protector main body 31A is folded back so as to be detached from the needle 21A (that is, toward the syringe 3) and relatively pivoted to the use position, and the protector 22A does not disturb the puncturing operation (see, for example, FIG. 12A). Then, the user pushes the protector main body 31A against the cylinder 11, and punctures a blood vessel or the like of the patient with the needle device 2 in this state.

Figure 12B:
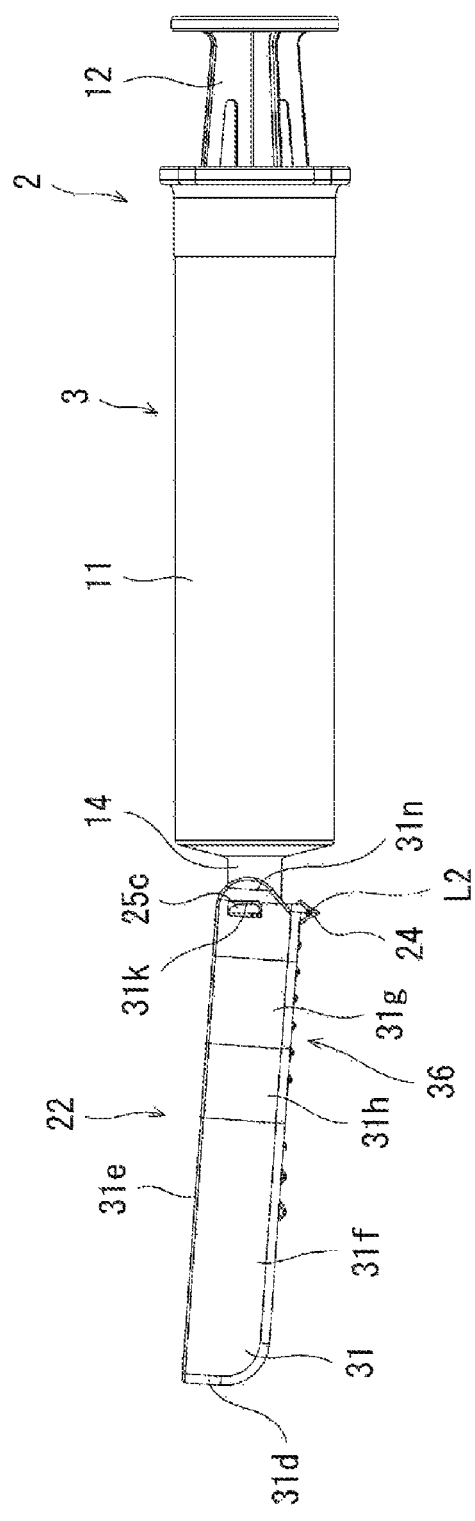
FIG. 12B is a view of the needle device of FIG. 8 in a protected state in which a needle tip is protected.

After administration of an infusion or blood collection is completed and the needle tip 21a is removed from a blood vessel or the like, the protector main body 31A is pivoted toward the needle 21A, and the needle 21A is covered with the protector main body 31A. When the protector main body 31A is further pivoted, the needle 21A comes into contact with the claw-like portion 34, so that the protector main body 31A is pivoted so as to be pushed. As a result, the claw-like portion 34 is pushed by the needle 21A and bent to the depth side to open the insertion groove 35 and push the protector main body 31A to the protection position, whereby the needle 21A passes through the lateral side of the claw-like portion 34 to enter the depth side of the insertion groove 35, and the needle 21A is housed in the insertion groove 35. As a result, the claw-like portion 34 elastically restores and returns to the initial position, and the insertion groove 35 is closed again by the claw-like portion 34. This suppresses detachment of the needle 21A in the insertion groove 35 from the opening 31e of the protector main body 31A, and the needle 21A is held in the protector main body 31A in a state where the needle 21A is covered with the protector main body 31A and the needle tip 21a is protected (see FIG. 12B). The needle assembly 1A is discarded with the protector main body 31A in this state. Therefore, it is possible to stop the needle from being discarded with the contaminated needle tip 21a being exposed, and it is possible to stop a user, a patient, a waste disposer or the like from getting stuck by the needle tip 21a to be infected with bacteria, viruses, etc.

In the needle assembly 1A to be discarded, an undesired load may act on the protector main body 31A depending on the discarding condition. That is, the protector main body 31A may be pushed to the depth side, or the protector main body 31A may be pushed to the near side. When pushed to the depth side, the protector main body 31A is pivoted from the protection position to the use position by such a load. However, since the pair of engagement holes 31j and 31k is engaged with the corresponding engagement pieces 25b and 25c, the protector main body 31A does not pivot by a predetermined angle or more, and the needle hub 23 is stopped from coming out of the protector main body 31A.

Figure 13:
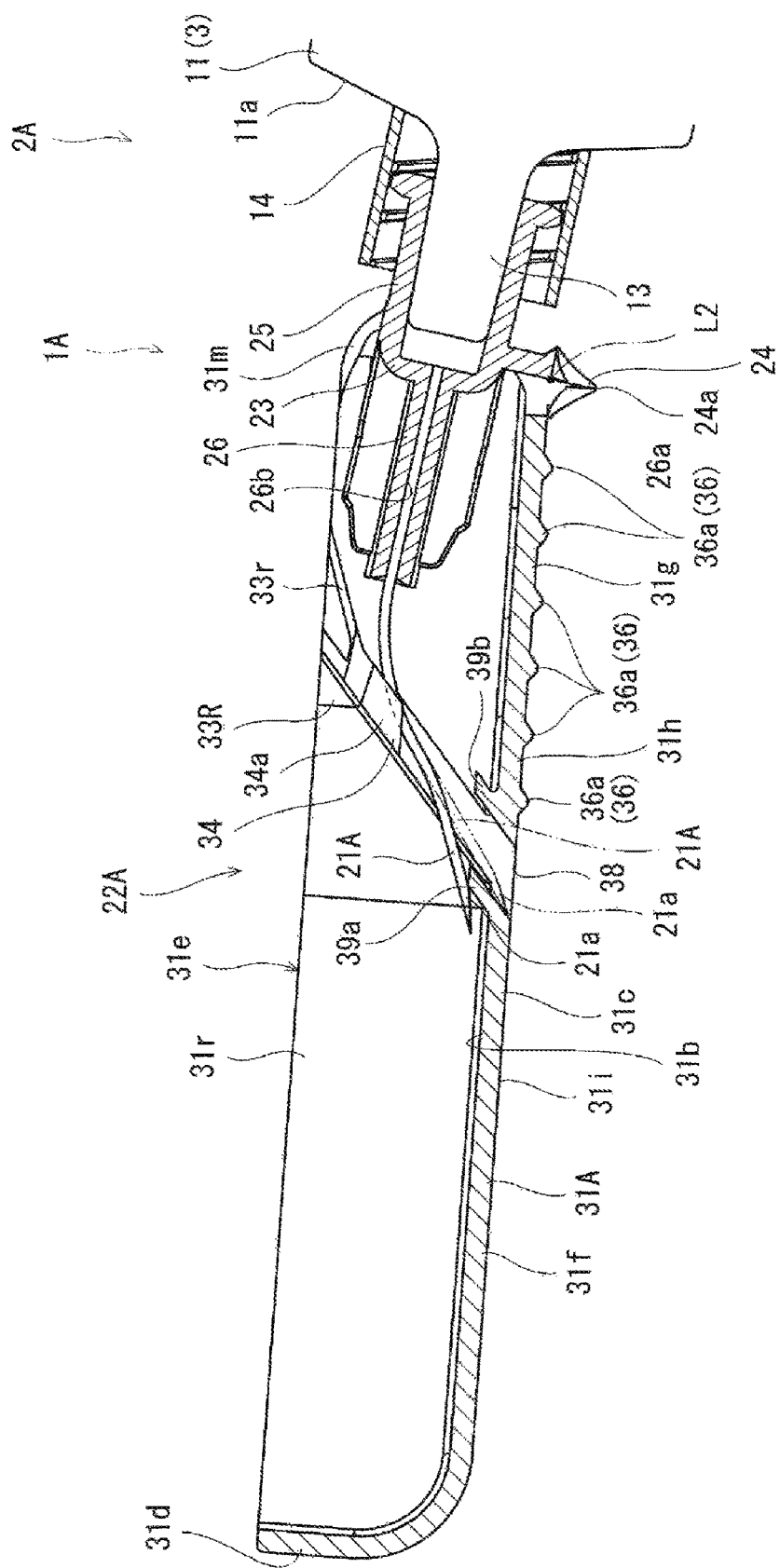
FIG. 13 is a view of the needle device of FIG. 8 with the needle bent by a claw-like portion.

The needle tip 21a of the needle 21A is also stopped from coming out of the protector main body 31A by the claw-like portion 34. That is, when the protector main body 31A pivots to the use position and the needle 21A moves to the opening 31e, the needle 21A contacts the claw-like portion 34 (see the needle 21A of the two-dot chain line in FIG. 11), and can not come out of the opening 31e of the protector main body 31A. On the other hand, since the needle 21A is brought into contact with the claw-like portion 34 to suppress the detachment of the needle 21A, a large load acts on the needle 21A so as to direct the needle tip 21a to the back face portion 31c. As described above, the needle 21A of the needle assembly 1A is formed to be thin, and the needle 21A is deformed (bent in more detail) such that the needle tip 21a is directed to the back face portion 31c by receiving an undesired load. As the protector main body 31A is pivoted, the deformation of the needle 21A becomes larger. As the deformation becomes larger, the needle tip 21a approaches the back face portion 31c and directs to the window 38. On the other hand, the barrier 39a is provided in the vicinity of the window 38, and as the needle 21A is deformed, the vicinity of the needle tip 21a eventually contact the one barrier 39a as shown in FIG. 13. The one barrier 39a is formed to project from the back face portion 31c, and can stop the movement of the needle tip 21a until the needle tip 21a passes over the one barrier 39a. Therefore, the one barrier 39a can stop the needle tip 21a from reaching the window 38. When the one barrier 39a is not present as in the safety needle assembly of Patent Literature 1, the needle tip 21a is easy to fall into the window 38 after the needle tip 21a slides along the back face portion 31c as shown by the two-dot chain line in FIG. 13.

Further, the one barrier 39a can provide sliding resistance to the needle 21A by contacting the bending needle 21A, and the needle 21A can be stopped from sliding along the one barrier 39a. That is, the needle tip 21a can be stopped from reaching the window 38. Since the one barrier 39a is formed to be inclined to the other side in the longitudinal direction, in the case where the needle tip 21a comes into contact with the one side face in the longitudinal direction of the one barrier 39a, the contact area between the needle tip 21a and the one barrier 39a can be increased, so that the movement can be further suppressed.

Furthermore, when the one barrier 39a contacts the vicinity of the needle tip 21a, the vicinity of the needle tip 21a of the needle 21A is supported. Thereby, when the protector main body 31A is further pivoted, the proximal end portion of the needle 21A starts to bend so as to warp in a direction away from the back face portion 31c. As a result, the needle tip 21a facing the back face portion 31c can rise, and the direction of the needle tip 21a can be deviated from the window 38. Therefore, even if the needle tip 21a passes over the one barrier 39a, the needle tip 21a can be made difficult to enter the window 38. In this way, by forming the one barrier 39a in the vicinity of the window 38, entry of the needle tip 21a into the window 38 can be suppressed. In the needle assembly 1A of the present embodiment, the one barrier 39a is formed adjacent to the window 38, but it does not have to be adjacent. That is, as long as the one barrier 39a is formed in the vicinity of the window 38 so that the needle tip 21a of the bending needle 21A contacts the one barrier 39a, the same effect can be obtained.

Next, a case where the protector main body 31A is pushed to the near side will be described. In this case, if the needle 21A is in a straight state, the needle tip 21a is located at the one side in the longitudinal direction with respect to the one barrier 39a, so that the vicinity of the needle tip 21a contacts the one barrier 39a or the back face portion 31c, and a certain distance can be maintained between the window 38 and the needle tip 21a. That is, the needle tip 21a can be away from the window 38, and the needle tip 21a can be stopped from entering the window 38.

Figure 14:
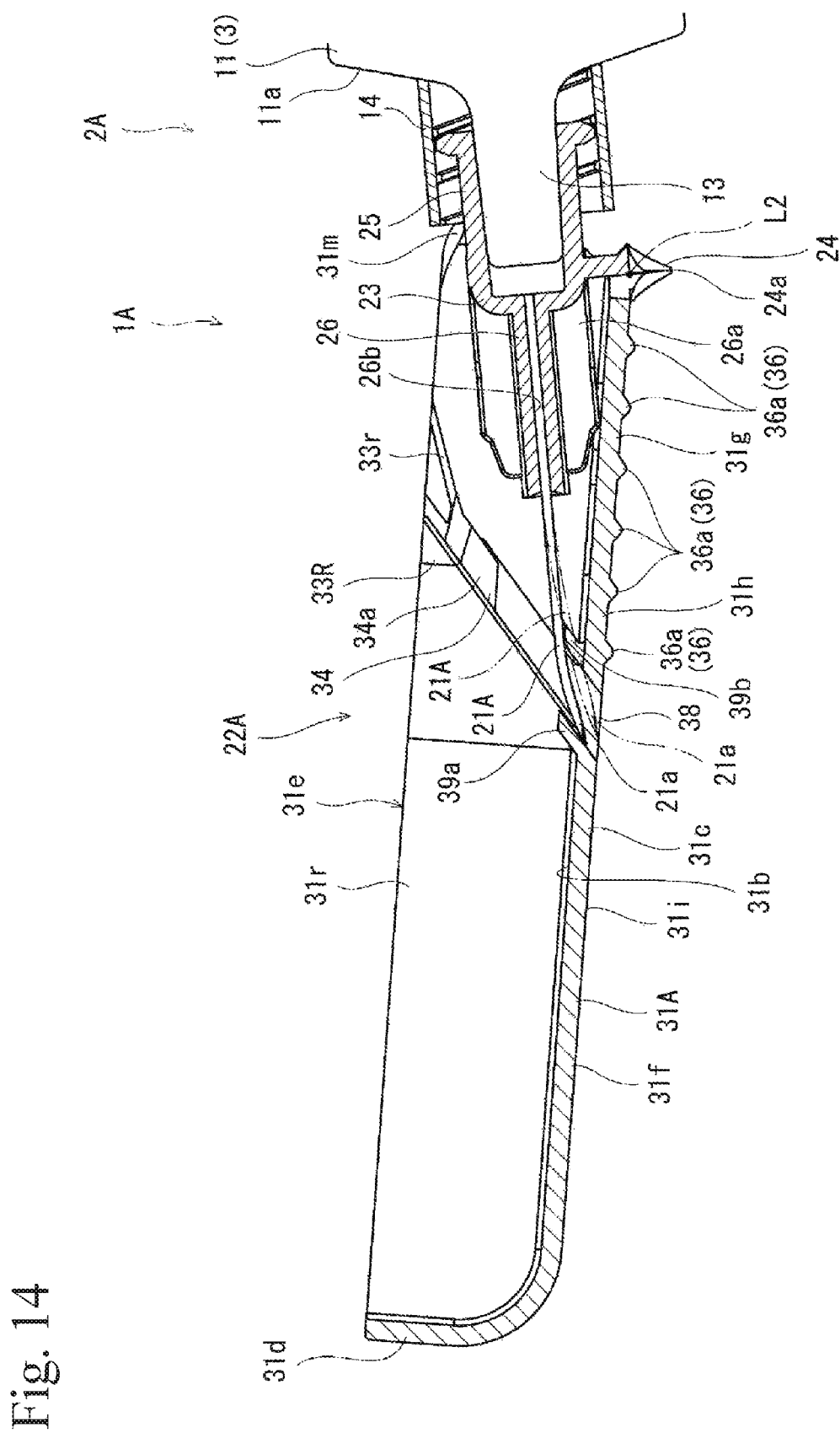
FIG. 14 is a view of the needle device of FIG. 8, showing the state in which a bent needle is stopped from coming out of a hole by a barrier.

On the other hand, after discarding the needle 21A, the needle 21A can not always be kept in a straight state, and depending on the discarding state, the needle 21A is bent such that the needle tip 21a is directed to the back face portion 31c and the needle tip 21a may be located further close to the window 38. In such a case, as shown in FIG. 14, the needle tip 21a may enter the window 38 without contacting the one barrier 39a and the back face portion 31c. Even in such a case, the other barrier 39b can support the middle portion of the needle 21A so that the needle 21A is away from the window 38, and it is possible to suppress entry of the needle tip 21a into the back of the window 38.

In the needle assembly 1A configured as described above, the pair of barriers 39*a* and 39*b* does not have to be formed adjacent to the window 38 as described above. On the other hand, by making the one barrier 39*a* adjacent to the window 38, when the needle 21A is bent by the claw-like portion 34, the needle 21A is short so that the needle tip 21*a* is not caught, stopping the needle tip 21*a* from falling into the window 38. On the other hand, by making the other barrier 39*b* adjacent to the window 38, the other barrier 39*b* can support the needle 21A so that the needle 21A is away from the back face portion 31*c* while suppressing its height. In addition, providing the pair of barriers 39*a* and 39*b* as in the needle assembly 1A of this embodiment does not limit the length of needle 21A, allowing the needle assembly for various applications to be available. That is, the highly versatile needle assembly 1A can be manufactured.

Other Embodiments

The needle assemblies 1, 1A of the first and second embodiments constitute the needle device 2 by attaching the syringe 3. However, the needle assembly does not have to have such a configuration. For example, a tube holder may be attached instead of the syringe 3. The tube holder is configured to attach a tube capable of containing an infusion, blood and the like, and includes, for example, a blood collection tube holder and the like. Further, the syringe 3 and the tube holder do not have to be separated from the needle hub 23 and may be integrally configured.

Moreover, in the needle assembly 1, 1A of the first and second embodiments, the protector main body 31, 31A is provided on the needle hub 23 via the plate-like hinge 24, but such a configuration is not essential. Any configuration is acceptable as long as the protector main body 31, 31A can be pivoted with respect to the needle hub 23 through the plate-like hinge 24 so as to protect the needle tip 21*a*. For example, the pivot ring is mounted on the needle hub 23 so as to be pivotable around the axis L1, and the protector main body 31, 31A is attached to the pivot ring so as to be pivotable around the pivot L2. As a result, the protector main body 31, 31A can be pivoted toward the needle 21, 21A, and can also be pivoted around the axis L1. Moreover, the protector main body 31, 31A does not have to be integrally formed with the needle hub 23 as described above, and may be configured separately from the needle hub 23. In this case, the protector 22, 22A is used by attaching the protector main body to a pivot ring mentioned above after use. In addition, the protector main body 31, 31A, the needle hub 23, and the needle 21, 21A do not have to have the shapes as described above. For example, the needle 21, 21A may be a bending needle whose distal portion is curved, and the shape of the protector main body 31, 31A may be changed accordingly.

Furthermore, in the needle assembly 1, 1A of the first and second embodiments, the claw-like portion 34 is inclined so as to extend to the depth side and the one side in the longitudinal direction as being closer to the inward side in the width direction, but it does not have to have such a shape. For example, the claw-like portion 34 may be inclined so as to extend to the depth side and the other side in the longitudinal direction as being closer to the inward side in the width direction. Also in this case, the claw-like portion 34 can be extended in the three-dimensional direction, and the linear distance L can be increased as compared with the case where the claw-like portion 34 is made to extend in the two-dimensional direction. Thus, the claw-like portion 34 can be bent with a smaller load. Further, the claw-like portion 34 does not have to extend to the depth side, and may extend so as to incline only in the width direction and the longitudinal direction, or may extend straight. Regardless of the shape, at least in the needle assembly 1, 1A according to the second embodiment, the window 38 is formed to form the claw-like portion 34 by the molding pin 37, and at least one of the barriers 39*a* and 39*b* is formed in accordance with the direction of the molding pin 37.

Further, in the needle assembly 1A of the second embodiment, the barriers 39*a* and 39*b* are provided on both sides in the longitudinal direction of the window 38, but both of the barriers 39*a* and 39*b* do not have to be provided. For example, in the case where the needle tip 21*a* is unlikely to enter the window 38 even when the back face portion 31*c* of the protector main body 31A is pushed in a state where the needle 21A is bent, the other barrier 39*b* may not be provided. Further, in the case where the needle tip 21*a* does not enter the window 38 when the protector main body 31A is pivoted to the depth side and the needle 21A is bent, the one barrier 39*a* may not be provided. Further, the claw-like portion 34 is not necessarily required, and there are various reasons why the needle 21A is bent other than bending due to the claw-like portion 34, and even in a case of bending other than bending due to the claw-like portion 34, the pair of barriers 39*a* and 39*b* can suppress entry of the needle tip 21*a* of the needle 21A into the back of the window 38.

REFERENCE CHARACTERS LIST 1, 1A needle assembly
2, 2A needle device
3 syringe (liquid transfer device)
21, 21A needle
21*a* needle tip
22, 22A protector
23 needle hub
24 hinge
31A protector main body
31*b* inner face
31*c* back face portion
31*e* opening
31*f* needle tip housing portion
31*g* hub housing portion
31*h* guide portion
31*i* back face
31*l*, 31*r* side face portion
33L, 33R guide rib (guide)
33*l*, 33*r* guide face
34 claw-like portion
38 window
39*a*, 39*b* barrier

The invention claimed is:

1. A needle assembly comprising:
a needle having an elongated body and a sharp needle tip at a tip end;
a needle hub provided at a base end of the needle; and
a protector is provided on the needle hub so as to be displaceable between a non-protection position at which the needle is exposed and a protection position at which the needle tip is protected by covering the needle,
wherein the protector comprises:
a protector main body having an elongated opening formed to match the needle, and allowing the needle to enter the protector main body from the opening to cover the needle tip when the protector is relatively displaced from the non-protection position to the protection position; and a claw-like portion provided on the protector main body such that the claw-like portion is bent by the needle when the protector is relatively displaced from the non-protection position to the protection position, allows the needle to advance into the protector main body, and is elastically restored to lock the needle when the needle enters the protector main body, and to stop the needle from escaping from an inside of the protector main body, and wherein the claw-like portion projects obliquely from the protector main body so as to extend in an inclined direction with respect to both a width direction and a longitudinal direction of the opening.

2. The needle assembly according to claim 1, wherein the claw-like portion extends in a depth direction of the protector, the depth direction being a direction orthogonal to the width direction and the longitudinal direction of the opening.

3. The needle assembly according to claim 1, wherein the claw-like portion extends to one side in a longitudinal direction directed from the base end of the needle to the needle tip in the protection position.

4. The needle assembly according to claim 1, further comprising:

a hinge pivotably attaching the protector main body to the needle hub, wherein the hinge is configured to relatively displace the protector from the non-protection position to the protection position by pivoting the protector main body, wherein the protector main body is formed in a U shape when cut at a plane perpendicular to the longitudinal direction so as to have a back face portion opposite the opening, and includes a needle tip housing portion at a tip end, the needle tip housing portion housing the needle tip entering the protector main body from the opening, and wherein the back face portion is formed smooth in an area corresponding to the needle tip housing portion.

5. The needle assembly according to claim 1, wherein the protector main body includes a needle tip housing portion capable of housing the needle tip entering the protector main body from the opening, a hub housing portion which is wider in the width direction than the needle tip housing portion and capable of housing the needle hub entering the protector main body from the opening, and a guide portion disposed between the needle tip housing portion and the hub housing portion, the guide portion guiding the needle to guide the needle tip into the needle tip housing portion, wherein the guide portion has a pair of opposing sides in a width direction of the guide portion, wherein the guide portion has a pair of guides projecting inward in the width direction from an inner face of each of the opposing sides, wherein the pair of guides is inclined toward an inward side in the width direction and an inside of the needle tip housing portion, and wherein the pair of guides is configured such that a tip end of the needle hub is disposed between the pair of guides when relatively displacing the protector to the protection position.

6. A needle device comprising:

the needle assembly according to claim 1; and a liquid transfer device configured to contain a liquid and attached to the needle hub so that an inside of the liquid transfer device is in communication with the needle.

7. A needle assembly comprising:

a needle having a sharp needle tip at a tip end;

a needle hub provided at a base end of the needle; and a protector having an elongated body formed to cover the needle, and provided on the needle hub so as to be displaceable between a non-protection position at which the needle is exposed and a protection position at which the needle tip is protected by covering the needle, wherein the protector has an opening for the needle to enter the protector when relatively displaced from the non-protection position to the protection position in one of four directions orthogonal to a longitudinal direction and orthogonal to each other, and a pair of side face portions and a back face portion to cover the needle in the protection position in remaining three directions, wherein a window and two barriers are formed on the back face portion of the protector, wherein the window is located near the needle tip of the needle when the protector is relatively displaced to the protection position, wherein the two barriers are formed near the window, are located near the needle tip of the needle in the protection position, and project from the back face portion so as to come into contact with the vicinity of the needle tip of the needle relatively displaced toward the window, wherein the protector includes a protector main body and a claw-like portion, wherein the claw-like portion is provided on one of the side face portions so as to project to one side of a width direction directed from the one of the side face portions to the other of the side face portions, and is bent by the needle when the protector is displaced from the non-protection position to the protection position, allows the needle to enter the protector main body, and is elastically restored to lock the needle when the needle passes over the claw-like portion, and to stop the needle from escaping from an inside of the protector main body, and wherein the two barriers are formed at a tip end and a base end of the protector relative to the window on the back face portion of the protector, and the two barriers and the window are closer to the tip end of the protector than the claw-like portion.

8. The needle assembly of claim 7, wherein the protector main body has the pair of side face portions and the back face portion, and allows the needle to enter the protector main body from the opening to cover the needle tip when the protector is relatively displaced from the non-protection position to the protection position, and wherein the window is directed to the claw-like portion to shape the claw-like portion.

9. The needle assembly according to claim 8, wherein the claw-like portion obliquely projects so as to approach the back face portion toward one side in the width direction and a tip end of the protector main body, wherein the window is formed obliquely toward a base end of the protector main body toward the claw-like portion, and wherein the two barriers are formed on the back face portion so as to be adjacent to the window and obliquely project toward the base end of the protector main body.

10. The needle assembly according to claim 7, wherein the needle tip of the needle and the two barriers are located closer to the tip end of the protector than the window in the protection position.

11. The needle assembly according to claim 7, wherein the needle tip of the needle and the two barriers are located closer to the base end of the protector than the window in the protection position.

12. A needle device comprising:
   the needle assembly according to claim 7; and
   a liquid transfer device configured to be capable of containing liquid and attached to the needle hub so that an inside of the liquid transfer device is in communication with the needle.

\* \* \* \* \*